US007662593B2

(12) United States Patent
Shigemori

(10) Patent No.: US 7,662,593 B2
(45) Date of Patent: Feb. 16, 2010

(54) ACTIVATION METHOD OF PROTEIN DERIVED FROM EXTREMELY THERMOPHILIC BACTERIUM IN NUCLEIC ACID AMPLIFICATION REACTION AND USE THEREOF

(75) Inventor: Yasushi Shigemori, Kisaradu (JP)

(73) Assignee: Aisin Seiki Kabushiki Kaisha, Kariya-shi (JP)

( * ) Notice: Subject to any disclaimer, the term of this patent is extended or adjusted under 35 U.S.C. 154(b) by 0 days.

(21) Appl. No.: 11/298,875

(22) Filed: Dec. 12, 2005

(65) Prior Publication Data
US 2006/0160115 A1    Jul. 20, 2006

(30) Foreign Application Priority Data
Dec. 21, 2004  (JP)  ............... 2004-368831

(51) Int. Cl.
C12P 19/34  (2006.01)
(52) U.S. Cl. .................................................. 435/91.2
(58) Field of Classification Search .................. None
See application file for complete search history.

(56) References Cited

U.S. PATENT DOCUMENTS

| 4,683,202 | A  | * | 7/1987  | Mullis .................... 435/91.2 |
| 5,223,414 | A  | * | 6/1993  | Zarling et al. ............. 435/91.2 |
| 5,510,473 | A  | * | 4/1996  | Camerini-Otero et al. .. 536/23.5 |
| 2003/0180746 | A1 | * | 9/2003 | Kmiec et al. ................ 435/6 |
| 2003/0219792 | A1 |   | 11/2003 | Armes et al. |

FOREIGN PATENT DOCUMENTS

| JP | 2004-222631 | 8/2004 |
| WO | WO 91/06679 | 5/1991 |
| WO | WO 94/14978 | 7/1994 |
| WO | WO 95/00666 | 1/1995 |
| WO | 2004/027060 A1 | 4/2004 |

OTHER PUBLICATIONS

Wetmur et al., "Cloning, Sequencing, and Expression of RecA Proteins from Three Distantly Related Thermophilic Eubacteria," J.Biol. Chem., 1994, vol. 269, No. 41, pp. 25928-25935.*
Kowalczykowski, S. Biochemistry, vol. 25, pp. 5872-5881, 1986.*
Evelina Angov, et al., "The recA Gene from the Thermophile *Thermus aquaticus* YT-1: Cloning, Expression, and Characterization", Journal of Bacteriology, vol. 176, No. 5, XP-002343424, Mar. 1994, pp. 1405-1412.
Michael J. Campbell, et al., "On the In Vivo Function of the RecA ATPase", Journal of Molecular Biology, vol. 286, No. 2, XP-004459763, Feb. 19, 1999, pp. 437-445.
Reika Watanabe, et al., "Interaction of *Escherichia coli* RecA Protein with ATP and Its Analogues", J. Biochem., vol. 116, No. 5, Apr. 14, 1994, pp. 960-966.
Christine Ellouze, et al., "Difference Between Active and Inactive Nucleotide Cofactors in the Effect on the DNA Binding and the helical Structure of RecA Filament Dissocation of RecA-DNA Complex by Inactive Nucleotides", Eur. J. Biochem., vol. 262, No. 1, Feb. 1999, pp. 88-94.

* cited by examiner

Primary Examiner—Gary Benzion
Assistant Examiner—Cynthia B Wilder
(74) Attorney, Agent, or Firm—Oblon, Spivak, McClelland, Maier & Neustadt, L.L.P.

(57) ABSTRACT

The present invention is to provide a method which makes it possible to activate RecA, and maintain its biological function in all the PCR cycles. Also, the invention is to provide a nucleic acid amplification method, and a kit for amplifying a nucleic acid which makes it possible to suppress non-specific amplification more specifically and efficiently to amplify only the desired nucleic acid. A method of activating a RecA protein derived from an extremely thermophilic bacterium in a polymerase chain reaction carried out in the presence of the RecA protein derived from the extremely thermophilic bacterium, wherein the RecA protein is activated by carrying out the reaction with the addition of nucleotide 5'-triphosphate (provided that the nucleotide 5'-triphosphate is neither deoxynucleotide 5'-triphosphate nor nucleotide 5'-O-3-thiotriphosphate).

2 Claims, 6 Drawing Sheets 1 2 3 4 5 6 rTaq buffer 7 8 9 10 11 12

T. th. RecA/
rTaq buffer 13 14 15 16 17 18

T. th. RecA/
Taq buffer 19 20 21 22 23 24

T. th. RecA+ATP/
rTaq buffer 1 2 3 4 5 6
T. th. RecA(+), ATP(+)

7 8 9 10 11 12
T. th. RecA(+), ATP(−)

1 2 3 4 5 6
T. th. RecA(+), ATP(+)

7 8 9 10 11 12
T. th. RecA(+), ATP(−)

1 2 3 4 5 6 7

T. th. RecA (+), ATP (+)

8 9 10 11 12 13 14

T. th. RecA (+), ATP (-)

15 16 17 18 19 20 21

T. th. RecA (-), ATP (-)

22 23 24 25 26 27 28

T. th. RecA storage buffer (+)
T. th. RecA (-), ATP (-)

29 30 31 32 33 34 35

T. th. RecA (-), ATP (+)

1 2 3 4 5 6 7 8 9 10 11 12 13 14 15

T. th. RecA(+), ATP(+)

16 17 18 19 20 21 22 23 24 25 26 27 28 29 30

T. th. RecA storage buffer(+)
T. th. RecA(−), ATP(−)

ACTIVATION METHOD OF PROTEIN DERIVED FROM EXTREMELY THERMOPHILIC BACTERIUM IN NUCLEIC ACID AMPLIFICATION REACTION AND USE THEREOF

CROSS REFERENCE TO RELATED APPLICATIONS

This application is based on and claims priority under 35 U.S.C. § 119 to Japanese Patent Application 2004-368831, filed on Apr. 16, 2004, the entire content of which is incorporated herein by reference.

BACKGROUND OF THE INVENT

1. Field of the Invention

The present invention relates to an activation method of a protein derived from an extremely thermophilic bacterium in a nucleic acid amplification reaction, and a nucleic acid amplification method and a kit for amplifying nucleic acids using the same.

2. Description of the Related Art

A polymerase chain reaction (Hereinafter, simply referred to as "PCR") is a remarkable technique which makes it possible to amplify a target specific DNA region 100,000 times or more in a short time. However, it is difficult to optimize the reaction. That is, the problem is that non-specific amplification occurs due to mis-priming such as annealing of the primer to sites other than the target sequence or annealing between primers. Therefore, it is needed to establish a technique which makes it possible to amplify the target DNA specifically. To achieve this, it is needed to control PCR so that no mis-priming occurs at each step of the PCR cycles.

In this regard, the hot start method is known as a method for making it difficult to cause non-specific amplification of nucleotide 5'-triphosphate. According to this method, a procedure is used such that a thermostable DNA polymerase does not undergo an extension reaction until the temperature reaches the annealing temperature or more. Specifically, the procedure is carried out by a method in which an antibody is bound to a DNA polymerase to inhibit the activity, or the like.

Also, recently, the present inventors reported that a RecA protein derived from an extremely thermophilic bacterium (hereinafter, simply referred to as "RecA") can interact with a template or a primer to promote binding of the primer only to a specific template sequence, thereby it can suppress mis-priming (for example, see WO 2004/027060). In the above-mentioned hot start method, the antibody protein used therein is denatured and deactivated in the first heating cycle of PCR. However, RecA suppresses mis-priming without losing its activity throughout the PCR cycles, which makes it possible to amplify only the specific PCR products.

Here, RecA is a protein which binds to a single-stranded nucleic acid cooperatively, searches a homologous region between the single-stranded nucleic acid and a double-stranded nucleic acid and undergoes homologous recombination of nucleic acids. Regarding RecA, various researches have been conducted for *Escherichia coli* (for example, see Watanabe R., et al., Interaction of *Escherichia coli* RecA protein with ATP and its analogues, J. Biochem., November 1994, Vol. 116, No. 5, pp. 960-966, and Ellouze C., et al., Difference between active and inactive nucleotide cofactors in the effect on the DNA binding and the helical structure of RecA filament dissociation of RecA-DNA complex by inactive nucleotides, Eur. J. Biochem., May 1999, Vol. 262, No. 1, pp. 88-94). For example, it has been reported that RecA requires ATP or dATP for its strand displacement activity, and the formation of a strong complex of RecA and DNA is necessary. Furthermore, it has been reported that adenosine 5'-O-3-thiotriphosphate has an influence on the strand displacement activity of RecA, and the contact between the chemical group at γ position of the nucleotide and the protein has an influence on the stability of a RecA-DNA complex.

However, these are all related to RecA derived from *Escherichia coli*, and there are almost no research reports on RecA derived from an extremely thermophilic bacterium which is used in the above-mentioned PCR technique reported by the present inventors. In addition, RecA derived from the extremely thermophilic bacterium and RecA derived from *Escherichia coli* are remarkably different in their properties, for example, resistance to a denaturant, thermostability, pH resistance, amino acid sequence and the like. Therefore, it was not possible to apply the technique for RecA derived from *Escherichia coli* as itself to RecA derived from the extremely thermophilic bacterium.

However, since in the PCR thermal denaturation is repeated under high temperature and the annealing temperature is high, even the thermostability of RecA derived from an extremely thermophilic bacterium is not sufficient. Thus, in the above-mentioned inventions that the present inventors reported previously, it was shown that the biological function possessed by RecA in the initial stage of PCR is reduced, and non-specific amplification occurs progressively through every cycle. At the same time, it was also shown that the biological function of RecA is reduced by a PCR reaction solution. As a result, mis-priming occurred and non-specific amplification was generated particularly at the later stages of the PCR cycles. Therefore, it was still required to establish a technique which makes it possible to control PCR further properly in each step of PCR.

In light of such circumstances, an object of the present invention is to provide a method which makes it possible to activate RecA and maintain its biological function in all the PCR cycles by improving the above-mentioned method. Furthermore, an object of the present invention is to provide a nucleic acid amplification method and a kit for amplifying nucleic acids, which makes it possible to suppress non-specific amplification more specifically and efficiently, and to amplify only a desired nucleic acid, by maintaining the biological function of RecA.

SUMMARY OF THE INVENTION

To solve the above-mentioned problems, the present inventors have studied extensively, and as a result, have found that non-specific binding can be suppressed effectively by carrying out PCR in the presence of NTP in addition to RecA, and only the desired nucleic acid can be amplified specifically. Furthermore, as a result of the extensive study, the present inventors have found that RecA can be activated in PCR by the presence of NTP, which makes it possible to maintain well its biological function. Based on these findings, the present invention has been completed.

Specifically, to achieve the above-mentioned object, the invention provides a method of activating a RecA protein derived from an extremely thermophilic bacterium in a polymerase chain reaction carried out in the presence of the RecA protein derived from the extremely thermophilic bacterium, wherein the RecA protein is activated carrying out the reaction with the addition of nucleotide 5'-triphosphate (provided that the nucleotide 5'-triphosphate is neither deoxynucleotide 5'-triphosphate nor nucleotide 5'-O-3-thiotriphosphate).

And, the nucleotide 5'-triphosphate is preferably selected from the group consisting of adenosine 5'-triphosphate, uridine 5'-triphosphate, guanosine 5'-triphosphate and cytidine 5'-triphosphate. Particularly preferably, the nucleotide 5'-triphosphate is adenosine 5'-triphosphate.

Furthermore, the RecA protein derived from the extremely thermophilic bacterium is preferably a RecA protein derived from *Thermus thermophilus*.

Furthermore, to achieve the above-mentioned object, the invention provides a nucleic acid amplification method of amplifying a target nucleic acid, which comprises carrying out a polymerase chain reaction in the presence of a RecA protein derived from the extremely thermophilic bacterium and nucleotide 5'-triphosphate (provided that the nucleotide 5'-triphosphate is neither deoxynucleotide 5'-triphosphate nor nucleotide 5'-O-3-thiotriphosphate).

And, the nucleotide 5'-triphosphate is preferably selected from the group consisting of adenosine 5 γ-triphosphate, uridine 5'-triphosphate, guanosine 5'-triphosphate and cytidine 5'-triphosphate. More preferably, the nucleotide 5'-triphosphate is adenosine 5'-triphosphate.

Furthermore, the RecA protein derived from the extremely thermophilic bacterium is preferably a RecA protein derived from *Thermus thermophilus*.

The target nucleic acid preferably has a region of an inhibitory or suppressive secondary structure.

Furthermore, the polymerase chain reaction is preferably a multiplex polymerase chain reaction.

And, to achieve the above-mentioned object, the present invention provides a detection method of a single nucleotide polymorphism, wherein the single nucleotide polymorphism is detected by screening amplification products amplified by the above-mentioned nucleic acid amplification method of the present invention.

Furthermore, to achieve the above-mentioned object, the present invention provides a kit for amplifying nucleic acids. The kit for amplifying nucleic acids according to the present invention is a kit for amplifying nucleic acids, comprising a DNA polymerase, four kinds of deoxynucleotide 5'-triphosphate corresponding to each of adenine, thymine, guanine and cytosine, a RecA protein derived from an extremely thermophilic bacterium, and nucleotide 5'-triphosphate (provided that the nucleotide 5'-triphosphate is neither deoxynucleotide 5'-triphosphate nor nucleotide 5'-O-3-thiotriphosphate).

And, the nucleotide 5'-triphosphate is preferably selected from the group consisting of adenosine 5'-triphosphate, uridine 5'-triphosphate, guanosine 5'-triphosphate and cytidine 5'-triphosphate. Particularly preferably, the nucleotide 5'-triphosphate is adenosine 5'-triphosphate.

Furthermore, the RecA protein derived from the extremely thermophilic bacterium is preferably a RecA protein derived from *Thermus thermophilus*.

And, the nucleic acid amplification is preferably based on a multiplex polymerase chain reaction.

EFFECTS OF THE INVENTION

The activation method of the RecA protein derived from the extremely thermophilic bacterium in the polymerase chain reaction according to the present invention has made it possible to activate the biological function of the RecA protein derived from the extremely thermophilic bacterium, and to maintain the activity further well in all the PCR cycles. As a result, RecA exerts its biological function effectively in PCR and suppresses mis-priming more effectively. Thereby, nucleic acids can be amplified more efficiently and specifically.

Therefore, according to the nucleic acid amplification method of the present invention, which uses the above-mentioned activation method of the present invention, mis-priming can be suppressed more effectively, making it possible to suppress non-specific amplification. As a result, nucleic acids can be amplified more efficiently and specifically.

DETAILED DESCRIPTION OF THE PREFERRED EMBODIMENTS

Figure 1:
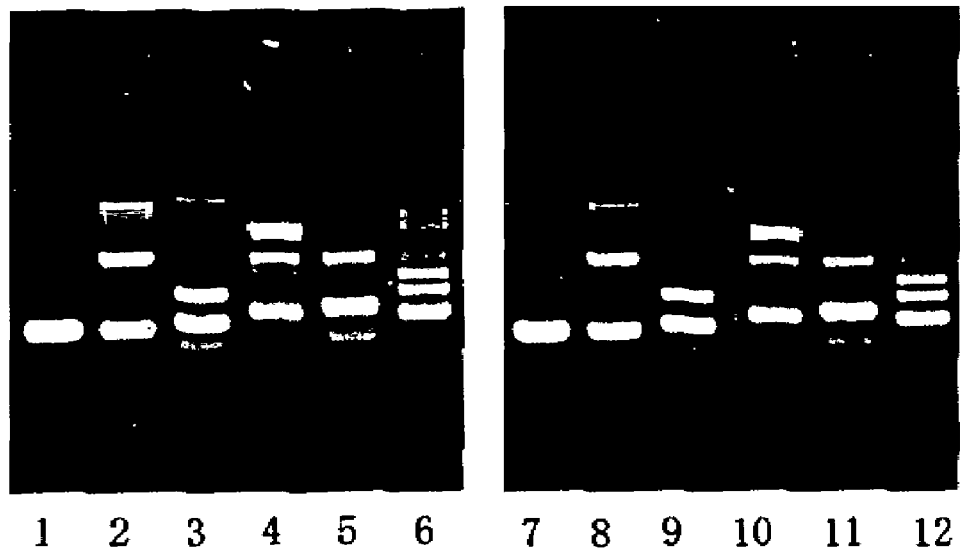
FIG. 1 is a drawing showing the results of Example 1 in which it was confirmed that the method of the present invention improved the decrease in performance of T. th. RecA by the composition of PCR reaction solution.
Figure 1:
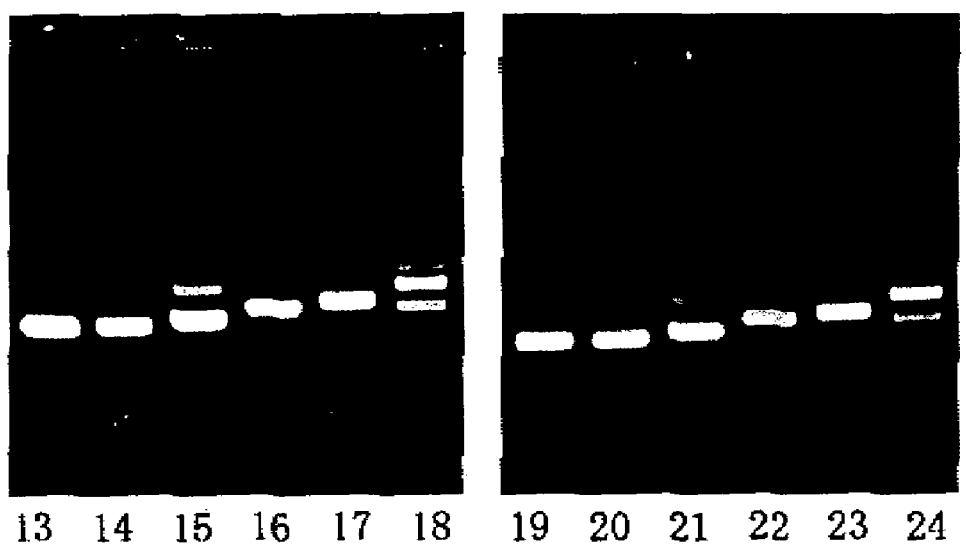

Specific embodiments of the present invention will be further illustrated below, which are only for illustration and do not limit the present invention.

The present invention provides a method of activating a RecA protein derived from an extremely thermophilic bacterium in PCR carried out in the presence of the RecA protein derived from the extremely thermophilic bacterium. The activation is made by carrying out the reaction with the addition of nucleotide 5'-triphosphate (provided that the nucleotide 5'-triphosphate is neither deoxynucleotide 5'-triphosphate nor nucleotide 5'-O-3-thiotriphosphate). The term "Activation of RecA" used in the present specification refers to maintaining RecA in a state in which the stability of RecA is improved and the biological function of RecA can be sufficiently exerted. The term "nucleotide 5'-triphosphate" in the present specification below refers to one that does not contain deoxynucleotide 5'-triphosphate and nucleotide 5'-O-3-thiotriphosphate, unless noted otherwise. Furthermore, nucleotide 5'-triphosphate in the present specification below, may be simply referred to as "NTP". Furthermore, deoxynucleotide 5'-triphosphate may be simply referred to as "dNTP", and nucleotide 5'-O-3-thiotriphosphate may be simply referred to as "NTPγS".

PCR will be explained below. PCR is a method of amplifying DNA in a chain reaction with a thermostable DNA polymerase. The principle of PCR is that a nucleic acid for amplification (hereinafter, simply referred to as a target nucleic acid) is amplified by $2^n$ times by repeating three steps of temperature changes in n cycles in the presence of primers and the thermostable DNA polymerase.

A PCR reaction solution in the present invention is prepared as a solution containing a target DNA, a thermostable DNA polymerase, primer DNA, dNTP and a suitable buffer in the presence of NTP and RecA. Here, the primer DNA and the dNTP may be labeled with a suitable labeling substance for detection if necessary. The labeling substance is known and can be suitably selected and used by the person skilled in the art.

Here, RecA is a protein which binds to a single-stranded nucleic acid cooperatively, searches a homologous region between the single-stranded nucleic acid and the double-stranded nucleic acid and undergoes the homologous recombination of nucleic acids. RecA used in the present invention is a protein derived from an extremely thermophilic bacterium. RecA which is suitably used in the present invention is, for example, RecA derived from the genus *Thermus*, the genus *Thermococcus*, the genus *Pyrococcus*, the genus *Thermotoga*, or the like. Specifically, RecA derived from *Thermus thermophilus* or *Thermus aquaticus* is exemplified. RecA derived from *Thermus thermophilus* is particularly preferable.

Such RecA also includes RecA which is artificially synthesized in a chemical synthesis or genetic engineering in addition to RecA derived from the nature. Specifically, it is possible to use RecA extracted from an extremely thermophilic bacterium according to the conventional method. Furthermore, it can be purified easily using a host/expression vector system such as the known *Escherichia coli*. For example, *Escherichia coli*, which are a host, is transformed by an expression vector to which a gene encoding the RecA is introduced by the known method and incubated, and the RecA is expressed. By homogenizing the host *Escherichia coli* and treating it with heat, proteins derived from *Escherichia coli* other than the RecA are thermally denatured and thermally aggregated, thereby they can be separated and removed by a centrifuge and the like. Thereby, the RecA, which is not thermally denatured, can be separated from the protein derived from *Escherichia coli* as a soluble fraction, and purified with affinity chromatography and the like.

In this case, the RecA is stable in the structure at room temperature since it is derived from an extremely thermophilic bacterium, and further has high stability to an organic solvent. This makes it possible to carry out the above-mentioned purification process at room temperature.

In addition, the host cell is not limited to *Escherichia coli*, but it is possible to use eukaryotic cells such as *Saccharomyces cerevisiae* and an insect (Sf9 cell) as the host cell. Also, any expression vector can be used as long as it can be expressed in the above-mentioned host cell, and includes a promoter sequence and a sequence such as a multi-cloning site having at least one restriction enzyme site into which a gene encoding RecA derived from the extremely thermophilic bacterium can be inserted. As the suitable promoter, for example, a T7lac promoter is preferably used.

Furthermore, the expression vector may include other known base sequences. The other known base sequences are not particularly limited. For example, it includes stability leader sequences which provide the stability of the expression product, a signal sequence which provide secretion of the expression product, and marking sequences which are capable of providing phenotypic selection in the transformed host such as a neomycin-resistant gene, a kanamycin-resistant gene, a chloramphenicol-resistant gene, an ampicillin-resistant gene, a hygromycin-resistant gene and the like. As such an expression vector, a commercially available expression vector for *Escherichia coli* (for example, pET protein expression system, manufactured by Novagen Inc.) can be used. In addition, an expression vector into which a suitable desired sequence is inserted, can be prepared and used.

Furthermore, it also includes a protein which has a structure similar to that of the above-mentioned RecA and is functionally equivalent. Thus, it is intended to also include a protein which is modified by artificial mutagenesis or gene recombination, in addition to naturally existing RecA-like proteins. For example, it may include a modified body which has an amino acid sequence in which one or more amino acids are substituted, deleted or added in an amino acid sequence of RecA derived from the nature, and further has the same biological function as the above-mentioned RecA. In addition, the number of variation in the amino acid sequence is not particularly limited as long as the original biological function of the protein is maintained.

Here, the modification for the amino acid sequence can be artificially carried out using known manipulation means for variation such as the method of site-specific mutagenesis or the like to an amino acid sequence to be modified (Nucleic Acid Res. 1982, 10, pp. 64-87). Furthermore, it also includes a modified body generated by variation of the amino acid in the nature.

NTP is a molecule in which three molecules of phosphoric acid are successively bonded by ester bonding to the hydroxyl group at 5-position of the ribose of the nucleotide in which a nucleic acid residue is bound with β glucoside bond to 1-position of D-ribofuranose. It is preferably, for example, adenosine 5'-triphosphate, uridine 5'-triphosphate, guanosine 5'-triphosphate and cytidine 5'-triphosphate. However, the NTP used in the present invention does not include dNTP. Therefore, deoxyadenosine 5'-triphosphate, deoxythymidine 5'-triphosphate, deoxyguanosine 5'-triphosphate and deoxycytidine 5'-triphosphate are excluded from the application to the present invention. Furthermore, nucleotide 5'-O-3-thiotriphosphate which is a nonhydrolyzable analogue of NTP is also similarly excluded from the application to the present invention. For the analogue excluded from the application, adenosine 5'-O-3-thiotriphosphate which is an analogue of adenosine 5'-triphosphate, and the like is exemplified.

As studied in Watanabe R., et al., Interaction of *Escherichia coli* RecA protein with ATP and its analogues, J. Biochem., November 1994, Vol. 116, No. 5, pp. 960-966, and Ellouze C., et al., Difference between active and inactive nucleotide cofactors in the effect on the DNA binding and the helical structure of RecA filament dissociation of RecA-DNA complex by inactive nucleotides, Eur. J. Biochem., May 1999, Vol. 262, No. 1, pp. 88-94, which show findings for RecA of *Escherichia coli*, the influence of nucleotides on RecA functions is various. Similarly, for RecA derived from the extremely thermophilic bacterium, it is presumed that the influence of nucleotides on RecA functions is various, and it is not possible to infer the influence by experience. In addition, in the present invention, RecA is efficiently activated by adding NTP in addition to dNTP which is incorporated into the synthesized nucleic acid and consumed in PCR as a substrate. Furthermore, nonhydrolyzable NTPγS such as ATPγS is not suitable for use in the invention in view of effective nucleic acid amplification.

In the present specification below, adenosine 5'-triphosphate, uridine 5'-triphosphate, guanosine 5'-triphosphate and cytidine 5'-triphosphate may be simply referred to as "ATP", "UTP", "GTP" and "CTP". In addition, deoxyadenosine 5'-triphosphate, deoxythymidine 5'-triphosphate, deoxyguanosine 5'-triphosphate and deoxycytidine 5'-triphosphate may be simply referred to as "dATP", "dTTP", "dGTP" and "dCTP". In addition, adenosine 5'-O-3-thiotriphosphate may be simply referred to as "ATPγS".

The target nucleic acid for amplification in the present invention is not limited in its origin, length and base sequence. It may be any one of either single-stranded or double-stranded nucleic acids. Specifically, it may be a genome DNA of an organism, or a fragment which is cleaved from the genome DNA by physical means or restriction enzyme digestion. Furthermore, a DNA fragment which is inserted into a plasmid, a phage or the like can be suitably used. Furthermore, it may be one that is prepared or isolated from a sample which possibly contains a nucleic acid. In addition, it may be any target nucleic acid such as artificial products such as a DNA fragment synthesized with a DNA automatic synthesizer which is commonly used in the related technical field, and a cDNA fragment synthesized with mRNA as a template.

Furthermore, the method of the present invention can be suitably utilized for amplifying a nucleic acid which has a region forming a secondary structure that inhibits or suppresses the nucleic acid amplification when general PCR is carried out. For example, it includes a template nucleic acid having high GC content or a template nucleic acid having short repeating sequences. They were an inhibitory factor in the nucleic acid amplification, since a higher order structure is formed when they become single stranded by thermal denaturation. According to the method of the present invention, RecA of which its biological function is well maintained by NTP, binds to a template nucleic acid. Thereby, it is possible to dissociate such higher order structure and amplify the template nucleic acid efficiently.

A primer is a sequence which is designed to be complementary to a specific sequence of a target nucleic acid. Particularly, it has preferably a base sequence complementary to both ends of the target sequence to be amplified. For the simplest system, two primers are required, but when multiplex PCR or the like is carried out, three or more primers may be used. Furthermore, only one primer may be used suitably for the amplification reaction. Design of the primer is determined by searching the sequence of the target nucleic acid in advance, except that a random primer is used. And, in searching the base sequence of the target nucleic acid, database such as GeneBank and EBI can be suitably used.

A primer may be prepared by a chemical synthesis based on the phosphoamidite method and the like, and when the nucleic acid to be targeted has been already acquired, its restriction enzyme fragment or the like can be used. When preparing the primer based on the chemical synthesis, it is designed based on sequence information of the target nucleic acid before synthesis. After the synthesis, the primer is purified by means such as HPLC. Furthermore, when carrying out the chemical synthesis, a commercially available automatic synthesizer can be also used. Here, the term complementary means that the primer and the target nucleic acid can specifically bind to each other according to the base-paring rule, and form a stable double-stranded structure. It encompasses not only complete complementarity, but also partial complementarity, which has only some nucleic acid bases suitably paired according to the base-pairing rule as long as the primer and the target nucleic acid can sufficiently form a stable double-stranded structure. The number of the bases should be large enough to recognize specifically the target nucleic acid, but conversely, if it is too large, it is not preferable since it may induce a non-specific reaction. Therefore, a suitable length is determined depending on many factors such as the sequence information of the target nucleic acid such as GC content, and hybridization reaction conditions such as reaction temperature and salt concentration in the reaction solution, but it is preferably 20 to 50 bases in length.

Here, the DNA polymerase to be used is not particularly limited as long as it is a thermostable DNA polymerase which can be usually used in PCR. For example, it includes a DNA polymerase derived from thermophilic bacteria such as a Taq polymerase derived from *Thermus aquaticus*, a T. th. polymerase derived from *Thermus thermophilus*, a Bst polymerase derived from *Bacillus Stearothermophilus*, Vent DNA polymerase derived from *Thermococcus litoralis*, a DNA polymerase derived from thermophilic Archaea such as a Pfu polymerase derived from *Pyrococcus furiosus* and the like.

For dNTP, four kinds of deoxynucleotide corresponding to each base of adenine, thymine, guanine and cytosine, are used. Particularly, a mixture of dGTP, dATP, dTTP and dCTP is preferably used. Furthermore, a derivative of deoxynucleotide may be also included as long as it can be incorporated by a thermostable DNA polymerase into a DNA molecule which is synthesized and extended in PCR. Such derivative is, for example, 7-deaza-dGTP, 7-deaza-dATP and the like, which can be used, for example, by replacing dGTP or dATP with them, or in the presence of both of them. Therefore, as long as four kinds are included corresponding to each base of adenine, thymine, guanine and cytosine which are necessary for nucleic acid synthesis, use of any derivative is not excluded.

The buffer solution is generally prepared by containing suitable buffer components, magnesium salts and the like. As the buffer components, Tris acetic acid, Tris-HCl, and a phosphate salt such as sodium phosphate and calcium phosphate can be suitably used, and particularly, Tris acetic acid is preferably used. The final concentration of the buffer components is adjusted in the range of 5 mM to 100 mM. Furthermore, pH of the buffer solution is adjusted preferably in the range of 6.0 to 9.5, more preferably 7.0 to 8.0. Furthermore, the magnesium salt is not particularly limited, but magnesium chloride, magnesium acetate and the like can be suitably used, and magnesium acetate is particularly preferable. Furthermore, if necessary, it is possible to add a potassium salt such as KCl and the like, DMSO, glycerol, betaine, gelatin, Triton and the like. In addition, it is possible to use a buffer solution which is accompanied in the commercially available thermostable DNA polymerase for PCR. The composition of the buffer solution can be suitably varied depending on the kind of the DNA polymerase to be used, or the like. Particularly, it can be suitably set, taking into consideration of the influence on the ionic strength of compounds such as $MgCl_2$, KCl and the like, the various additives such as DMSO, glycerol and the like that may affect the melting point of DNA, and the concentration of the additives. Particularly, the method of the present invention can improve resistance of RecA to a PCR reaction solution as shown in Example 2. Therefore, in the present invention, it is possible to use the PCR reaction solution in a broad range of the composition.

And, the reaction solution is preferably prepared in a volume of 100 µl or less, particularly in the range of 10 to 50 µl. For the concentration of each component, nucleotide 5'-triphosphate is contained preferably 50 µM or more in the reaction system, particularly preferably 400 µM or more, but it is preferably prepared as 1 mM or less in view of economic efficiency and the like. RecA is preferably used to be contained with the concentration of 0.004 to 0.02 µg/µl in the reaction solution. Concentrations of the components other than RecA can be suitably set by the person skilled in the art since PCR is known. For example, the target nucleic acid is preferably prepared in a concentration of 10 pg to 1 µg per 100 µl, and the primer DNA is preferably prepared in a final concentration of 0.01 to 10 µM, particularly 0.1 to 1 µM. Furthermore, the DNA polymerase is preferably used in a concentration of 0.1 to 50 Units, particularly 1 to 5 Units per 100 μl. And, dNTP is preferably prepared in a final concentration of 0.1 mM to 1 M. In addition, the magnesium salt is preferably prepared in a final concentration of 0.1 to 50 mM, particularly 1 to 5 mM.

PCR is carried out according to the following steps, and these steps are carried out in the presence of RecA and NTP.
(1) Thermal denaturation of template nucleic acid
(2) Annealing of primer
(3) Extension reaction by thermostable polymerase By repeating suitable times the reaction consisting of the three step temperature change of the above-mentioned (1) to (3) as one cycle, synthesis of the other nucleic acid chain having complementarity is initiated with the primer as a starting point and the target nucleic acid as a template. As a result, the target nucleic acid is amplified by $2^n$ times with the reactions of n cycles. The thermocycle number is determined depending on the kind, amount, purity and the like of the target nucleic acid as a template, but preferably 20 to 40 cycles, particularly 32 to 36 cycles from a viewpoint of the efficient nucleic acid amplification and suppression of the non-specific amplification. Particularly, the method of the present invention makes it possible to keep the activity of RecA by maintaining well the functions of RecA even after the PCR cycle numbers. Therefore, it can be also applied to high-cycle PCR.

Each step will be illustrated below.

(1) Thermal Denaturation of Template Nucleic Acid

A double-stranded nucleic acid is denatured and dissociated to single stranded one by heating. Preferably, it is carried out at 92 to 98° C. for 10 to 60 seconds. In addition, in the case where a long DNA region is amplified, only the first thermal denaturation can be set to a low temperature (for example, 92° C. or so) in order to prevent dissociation of the template DNA.

(2) Annealing of Primer

By lowering the temperature, a hybrid is formed between the template nucleic acid which has been thermally denatured and become single stranded one in the above-mentioned (1), and the primer. The annealing is preferably carried out for 30 to 60 seconds. In addition, the annealing temperature is preferably set as Tm of the oligonucleotide used as the primer after estimating the Tm. Usually, it is carried out at 50 to 70° C.

(3) Extension Reaction by Thermostable Polymerase

An extension reaction of a nucleic acid strand at a primer is carried out by a thermostable polymerase at the 3' end. The extension reaction temperature is suitably set depending on the kind of the thermostable polymerase, and the reaction is preferably carried out at 65 to 75° C. In addition, when the target sequence is 1 kb or less, the extension time is sufficient with about 1 minute. When the target sequence is more than the above range, it is preferably elongated at a rate of 1 minute per 1 kb.

By the constitution as described above, in PCR which is carried out in the presence of RecA derived from the extremely thermophilic bacterium, the activation of the RecA is achieved and the biological function of RecA is maintained. This is considered to be due to the reason that in the presence of NTP, the stability of the biological function of RecA against external factors can be improved. Particularly, it is considered that NTP has a role of improving the thermostability of RecA, improving resistance of RecA to a PCR reaction solution, and the like. That is, in the presence of NTP in PCR, the function of RecA derived from the extremely thermophilic bacterium is well maintained throughout all the PCR cycles. As a result, the nucleic acid can be amplified efficiently and specifically.

Therefore, the present invention also provides a nucleic acid amplification method of amplifying a target nucleic acid by carrying out a polymerase chain reaction in the presence of RecA derived from an extremely thermophilic bacterium and NTP (provided that the NTP is neither dNTP nor NTPγS).

According to the nucleic acid amplification method of the present invention, it is possible to suppress non-specific amplification through all the cycles and amplify nucleic acids efficiently as well. As described above, this is considered to be due to the reason that in the presence of NTP, the stability of the biological function of RecA against external factors can be improved. Particularly, it is considered that NTP has a role of improving the thermostability of RecA, improving resistance to a PCR reaction solution, and the like. That is, in the presence of NTP, the functions of RecA are well maintained and activated throughout all the PCR cycles. Therefore, it is possible to maintain a state in which the sequence specificity of the primer to the template nucleic acid is improved throughout all the PCR cycles. As a result, by the function of RecA in all the PCR cycles, it is possible to suppress non-specific amplification due to mis-priming such as annealing of the primer to sites other than the target sequence or annealing between the primers. In addition, by the presence of NTP, consumption of dNTP in PCR can be suppressed to a minimum, which makes efficient PCR amplification possible.

And, the amplification method of the present invention may be used in various uses. For example, it may be used in many fields such as the medical field, the biochemical field, the environmental field, the food field and the like. Specifically, as a use in the medical field, it includes gene diagnosis commencing with the detection of a single nucleotide polymorphism, the detection of a pathogen such as a virus or a bacterium like SARS and influenza, and the like. In addition, as a use in the biochemical field, it includes the identification of individuals, the identification of organic species such as the certification of fake brand food, and the like. In addition, as a use in the environmental field, it includes environmental measurements such as the detection of the pathogen such as viruses or bacteria in the environment, a search for novel useful microorganisms, and the like. In addition, as a use in the food field, it includes the examination whether or not the food contains genetically modified organisms. However, it is not limited thereto. The method of the present invention can be applied without limitation if it is a use to which PCR can be applied.

Among them, the present invention also provides a detection method of a single nucleotide polymorphism. In the detection method of the single nucleotide polymorphism according to the present invention, the single nucleotide polymorphism is detected by screening amplification products amplified by the nucleic acid amplification method of the present invention as described above. By amplifying the nucleic acid in the presence of NTP in addition to RecA, the amplification method of the present invention makes it possible to suppress non-specific bonding between the template DNAs of the primer and between the primers. Since this effect is maintained in all the PCR cycles, it is possible to suppress mis-priming of the primer effectively. Therefore, by using the primer which is complementary to the nucleic acid having the desired single nucleotide polymorphism, the nucleic acid having the single nucleotide polymorphism can be efficiently amplified. On the other hand, the nucleic acid not having the single nucleotide polymorphism is not amplified or its amplification is suppressed, thereby it is possible to amplify specifically the nucleic acid having the single nucleotide polymorphism. Therefore, it is possible to detect the single nucleotide polymorphism with good sensitivity and efficiency.

The present invention also provides a kit for nucleic acid amplification to amplify nucleic acids by PCR. The kit for amplifying nucleic acids of the present invention comprises a DNA polymerase, dNTP, RecA derived from an extremely thermophilic bacterium and NTP. Furthermore, it may suitably contain components necessary for PCR, such as a suitable buffer solution, a magnesium salt and the like. In addition, in the case of a kit for detecting a pathogen having the desired nucleic acid, any primer specific for amplifying the desired nucleic acid may be contained. By comprising such components necessary for PCR amplification as a kit, simple and quick PCR amplification is possible.

Other Embodiments

The nucleic acid amplification method of the present invention can be used by various modified methods of PCR. For example, it includes adaptor ligation PCR, mutant allele-specific amplification method (MASA method), asymmetric PCR, inverse PCR (IPCR), reverse transcription PCR (RT-PCR), PCR-single strand conformation polymorphism (PCR-SSCP method), arbitrarily primed PCR (AP PCR), RACE, multiplex PCR or the like. However, it is not limited thereto, and it can be used in all the modified methods of PCR.

Particularly, use in the multiplex PCR is a preferable example. Since the method of the present invention makes PCR amplification possible with a state in which the activity of RecA which is a homologous recombinant protein, is maintained, the sequence specificity of the template DNA to the primer is improved. Therefore, since specific amplification is made possible in response to the presence of the target nucleic acid, the method of the present invention can be suitably used in the multiplex PCR that uses a plurality of primers. The term Multiplex PCR is a method in which a plurality of target sequences of the target nucleic acid are simultaneously amplified in one reaction vessel. A primer set capable of amplifying each of the target sequences is put into one reaction vessel, and amplified by single PCR manipulation. By using the primer set capable of amplifying a plurality of target sequences, it is possible to reduce significantly time, labor and cost of a reagent which are required for amplification of the target DNA compared to single PCR. Furthermore, since even a trace of a sample can also be handled as a subject and manipulation is simple, the present method can be used in applications at an on-site level.

Furthermore, the present invention provides a kit for amplifying nucleic acids in order to provide in a multiplex PCR reaction. The kit for amplifying nucleic acids comprises a DNA polymerase, dNTP, RecA derived from an extremely thermophilic bacterium and NTP. Furthermore, it may suitably contain components necessary for PCR, such as a suitable buffer solution, a magnesium salt and the like. In addition, in the case of a kit for detecting a pathogen having the desired nucleic acid, any primer which is specific for amplifying the desired nucleic acid may be included. Furthermore, a necessary detection device may be included. By comprising such components necessary for multiplex PCR amplification as a kit, further simple and quick PCR amplification is possible and availability in the medical scene and the like is improved.

EXAMPLES

Hereinafter, Examples will be described below, and the present invention will be illustrated in more detail. However, the present invention is not limited to these examples.

Reagent

Reagents used in the following experiments will be explained.

A genome DNA (Human genomic DNA, Catalogue No. G3041, manufactured by Promega) was used as a template.

An rTaq-HS polymerase (manufactured by Takara Bio Inc.), an ExTaq-HS polymerase (manufactured by Takara Bio Inc.) or a T. th. DNA polymerase (Product No. N8080187, manufactured by Applied Biosystems) was used as a DNA polymerase.

RecA derived from *Thermus thermophilus* (hereinafter, simply referred to as T. th. RecA) was used as RecA. T. th. RecA was prepared and used by the present inventors referring to the description of Masui R, Mikawa T, Kato R, Kuramitsu S., Characterization of the oligomeric states of RecA protein: monomeric RecA protein can form a nucleoprotein filament., Biochemistry, 20 Oct. 1998, Vol. 37, No. 42, pp. 14788-14797.

In addition, as ATP, GTP, UTP and CTP, the products of Roche Diagnostics K.K. (Product No. 1277057) were used.

Sequences of the primer sets used here will be shown below.

```
Primer Set 1:
5'-ACAATGGGCTCACTCACCC            (SEQ ID NO. 1)

5'-CTAAGACCAATGGATAGCTG           (SEQ ID NO. 2)

Definition: Human DNA sequence
from clone RP11-392N11 on
chromosome 9
GenBank Acc. No. AL359181

Primer Set 2:
5'-GCTCAGCATGGTGGTGGCATAA-3'      (SEQ ID NO. 3)

5'-CCTCATACCTTCCCCCCCATTT-3'      (SEQ ID NO. 4)

Definition: Homo sapiens CYP21
gene
GenBank Acc. No. M12792 M23280

Primer Set 3:
5'-GACTACTCTAGCGACTGTCCATCTC-3'   (SEQ ID NO. 5)

5'-GACAGCCACCAGATCCAATC-3'        (SEQ ID NO. 6)

Definition: Human S100 protein
beta-subunit gene
GenBank Acc. No. M59486

Primer Set 4:
5'-AACCTCACAACCTTGGCTGA-3'        (SEQ ID NO. 7)

5'-TTCACAACTTAAGATTTGGC-3'        (SEQ ID NO. 8)

Definition: Homo sapiens
chromosome 8
GenBank Acc. No. AC103819

Primer Set 5:
5'-AGGCAACTAGGATGGTGTGG-3'        (SEQ ID NO. 9)

5'-CAGGGAGCGTGTCCATAGG-3'         (SEQ ID NO. 10)
```

Definition: *Homo sapiens*
glyceraldehyde-3-phosphate
dehydrogenase (GAPD) gene
GenBank Acc. No. AY340484

Primer Set 6:
5'-CTGCTGAAAGAGATGCGGTGG-3'    (SEQ ID NO. 11)

5'-AGGAAAACAGCCCAAGGGACAG-3'   (SEQ ID NO. 12)

Definition: Human beta globin
region on chromosome 11
GenBank Acc. No. U01317

Primer Set 7:
5'-CACATCAATGTTGTTGTTT-3'      (SEQ ID NO. 13)

5'-TTCCTTGTCTCCCCAAGTTC-3'     (SEQ ID NO. 14)

Definition: *Homo sapiens*
chromosome 11, clone
RP11-1205H24
GenBank Acc. No. AC129505

Primer Set 8:
5'-ACTTTGTTCTGAGCCTCACA-3'     (SEQ ID NO. 15)

5'-GTTGCCCAATCGCCCCTCTC-3'     (SEQ ID NO. 16)

Definition: *Homo sapiens*
transferrin (TF) gene
GenBank Acc. No. AY308797

Primer Set 9:
5'-AACCTGACTAGAAAAGCTAT-3'     (SEQ ID NO. 17)

5'-GAATGAGTGGTTAATTAATT-3'     (SEQ ID NO. 18)

Definition: *Homo sapiens*
clone NGR0524 mitochondrion,
partial genome
GenBank Acc. No. AF465941

Primer Set 10:
5'-CTCTA GCGACTGTCC ATCTC-3'   (SEQ ID NO. 19)

5'-GACAG CCACCAGATC CAATC-3'   (SEQ ID NO. 20)

Definition: Human S100 protein
beta-subunit gene
GenBank Acc. No. M59486

Primer Set 11:
5'-GACTACTCTA GCGACTGTCC ATCTC-3'   (SEQ ID NO. 21)

5'-GACTGGACAG CCACCAGATC CAATC-3'   (SEQ ID NO. 22)

Definition: Human S100 protein
beta-subunit gene
GenBank Acc. No. M59486

Primer Set 12:
5'-TTAAA GACTACTCTA GCGACTGTCC ATCT(SEQ ID NO. 23)
C-3'

5'-CATTA GACTGGACAG CCACCAGATC CAAT(SEQ ID NO. 24)
C-3'

Definition: Human S100 protein
beta-subunit gene
GenBank Acc. No. M59486

Primer Set 13:
5'-GTGGATTAAA GACTACTCTA GCGACTGTC (SEQ ID NO. 25)
C ATCTC-3'

5'-TATCCCATTA GACTGGACAG CCACCAGAT (SEQ ID NO. 26)
C CAATC-3'

Definition: Human S100 protein
beta-subunit gene
GenBank Acc. No. M59486

Primer Set 14:
5'-GTTGT GTGGATTAAA GACTACTCTA GCG (SEQ ID NO. 27)
ACTGTCC ATCTC-3'

5'-AATCT TATCCCATTA GACTGGACAG CCA (SEQ ID NO. 28)
CCAGATC CAATC-3'

Definition: Human S100 protein
beta-subunit gene
GenBank Acc. No. M59486

Primer Set 15:
5'-TTCCTGTTGT GTGGATTAAA GACTACTCT (SEQ ID NO. 29)
A GCGACTGTCC ATCTC-3'

5'-GTTTTAATCT TATCCCATTA GACTGGACA (SEQ ID NO. 30)
G CCACCAGATC CAATC-3'

Definition: Human S100 protein
beta-subunit gene
GenBank Acc. No. M59486

Primer Set 16:
5'-GCAGC TTTCATGGGC ACTGT-3'   (SEQ ID NO. 31)

5'-CAGGG CTGGACTGAC ATTTG-3'   (SEQ ID NO. 32)

Definition: *Homo sapiens* blue cone
opsin gene
GenBank Acc. No. L32835

Primer Set 17:
5'-TCCAGGCAGC TTTCATGGGC ACTGT-3'  (SEQ ID NO. 33)

5'-AGAGACAGGG CTGGACTGAC ATTTG-3'  (SEQ ID NO. 34)

Definition: *Homo sapiens* blue cone
opsin gene
GenBank Acc. No. L32835

Primer Set 18:
5'-CTACC TCCAGGCAGC TTTCATGGGC ACT (SEQ ID NO. 35)
GT-3'

5'-CACAG AGAGACAGGG CTGGACTGAC ATT (SEQ ID NO. 36)
TG-3'

Definition: *Homo sapiens* blue cone
opsin gene
GenBank Acc. No. L32835

Primer Set 19:
5'-GCCTTCTACC TCCAGGCAGC TTTCATGGG (SEQ ID NO. 37)
C ACTGT-3'

5'-GYAAGCACAG AGAGACAGGG CTGGACTGA (SEQ ID NO. 38)
C ATTTG-3'

Definition: *Homo sapiens* blue cone
opsin gene
GenBank Acc. No. L32835

Primer Set 20:
5'-TCTGG GCCTTCTACC TCCAGGCAGC TTT (SEQ ID NO. 39)
CATGGGC ACTGT-3'

5'-GTGGA GYAAGCACAG AGAGACAGGG CTG (SEQ ID NO. 40)
GACTGAC ATTTG-3'

Definition: *Homo sapiens* blue cone
opsin gene
GenBank Acc. No. L32835

Primer Set 21:
5'-CCCTGTCTGG GCCTTCTACC TCCAGGCAG (SEQ ID NO. 41)
C TTTCATGGGC ACTGT-3'

-continued

5'-ATCGGGTGGA GYAAGCACAG AGAGACAGG G CTGGACTGAC ATTTG-3' (SEQ ID NO. 42)

Definition: Homo sapiens blue cone opsin gene
GenBank Acc. No. L32835

Primer Set 22:
5'-CCCACGATCAATGCCATCAACT-3' (SEQ ID NO. 43)

5'-CGGTGAGAGGCACTGCCAGATT-3' (SEQ ID NO. 44)

Definition: Homo sapiens
chromosome 10 clone RP11-124L5
GenBank Acc. No. AC022389

Primer Set 23:
5'-GCTCGCTTTCTTGCTGTCCAAT-3' (SEQ ID NO. 45)

5'-GCCCTTCATAATATCCCCCAGTTT-3' (SEQ ID NO. 46)

Definition: Human beta globin
region on chromosome 11
GenBank Acc. No. U01317

Primer Set 24:
5'-GTCCTTCCCCCGCTGGAAAC-3' (SEQ ID NO. 47)

5'-GCAGCAGAGATCATCGCGCC-3' (SEQ ID NO. 48)

Definition: Homo sapiens MYC gene
GenBank Acc. No. X00364

Primer Set 25:
5'-GTGGGGTGCTGGGAGTTTGT-3' (SEQ ID NO. 49)

5'-TCGGACAGAAACATGGGTCTGAA-3' (SEQ ID NO. 50)

Definition: Homo sapiens neural
retinal-specific leucine zipper
protein (NRL) gene
GenBank Acc. No. U95012

Primer Set 26:
5'-GGTGCTCAGAACCCCCACAATC-3' (SEQ ID NO. 51)

5'-CCTACCGACCCCATTCCACTCT-3' (SEQ ID NO. 52)

Definition: Homo sapiens growth
hormone locus on chromosome 17
GenBank Acc. No. NG_001334

Primer Set 27:
5'-CACAGATTTCCAAGGATGCGCTG-3' (SEQ ID NO. 53)

5'-CGTGCTCTGTTCCAGACTTG-3' (SEQ ID NO. 54)

Definition: Homo sapiens
interleukin 9 receptor (IL9R) gene
GenBank Acc. No. AY071830

Primer Set 28:
5'-CGTCTGGCGATTGCTCCAAATG-3' (SEQ ID NO. 55)

5'-GGGCAGTTGTGATCCATGAGAA-3' (SEQ ID NO. 56)

Definition: Homo sapiens SVMT gene
for synaptic vesicle monoamine
transporter
GenBank Aco. No. AB044401

Primer Set 29:
5'-GGCTTGCACCAGCTTAGGAAAG-3' (SEQ ID NO. 57)

5'-CGTTAGGCATAATCAGTGGGATAGT-3' (SEQ ID NO. 58)

Definition: Homo sapiens
chromosome 11
GenBank Acc. No. AC129505

-continued

Primer Set 30:
5'-GCCTCTGATTCCTCACTGATTGCTCT-3' (SEQ ID NO. 59)

5'-TGTCAACCACCCTTAACCCCTCC-3' (SEQ ID NO. 60)

Definition: Homo sapiens p53 gene
GenBank Acc. No. X54156

Primer Set 31:
5'-TTGGAGGGGTGGGTGAGTCAAG-3' (SEQ ID NO. 61)

5'-GGAGGGGTGGGGGTTAATGGTTA-3' (SEQ ID NO. 62)

Definition: Human hepatocyte
nuclear factor 4-alpha gene
GenBank Acc. No. U72959

Primer Set 32:
5'-GGAACAAGACACGGCTGGGTT-3' (SEQ ID NO. 63)

5'-AGCAAGGCAGGGCAGGCAAGT-3' (SEQ ID NO. 64)

Definition: Human midkine gene
GenBank Acc. No. D10604

Primer Set 33:
5'-CGGTCCCATTCTCAGGGAATCT-3' (SEQ ID NO. 65)

5'-GCCCAGAGGAAGAAGAAGGAAA-3' (SEQ ID NO. 66)

Definition: Human rhodopsin gene
GenBank Acc. No. U49742

Example 1

Improvement of Decrease of T. th. RecA Protein Performance by the Composition of a PCR Reaction Solution The influence of the composition of a PCR reaction solution on the performance of a T. th. RecA was confirmed. Also, it was confirmed that the performance of the T. th. RecA protein can be maintained by the presence of ATP.

Method

The PCR amplification reaction was carried out using a human genome DNA as a template and Primer Set 1. Four kinds of PCR reaction solution were prepared as shown below. Specifically, Reaction solution A was prepared by using 1×rTaq buffer (manufactured by Takara Bio Inc.) as a buffer solution, and Reaction solution B was prepared by adding T. th. RecA further to Reaction solution A. Reaction solution C was prepared by using Taq buffer (manufactured by Takara Bio Inc.) as a buffer solution and adding T. th. RecA. Reaction solution D was prepared by adding T. th. RecA and ATP further to Reaction solution A. The composition of each of the reaction solutions is as shown below. As a DNA polymerase, an rTaq-HS polymerase (manufactured by Takara Bio Inc.) was used.

Reaction Solution A:
0.8 µM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
The above materials were mixed in a 1×rTaq buffer to make a total volume of 25 µl.

Reaction Solution B:
0.8 µM (the final concentration) Primer set
25 ng Template DNA 0.7 unit DNA polymerase
0.2 mM (the final concentration) dNTP mixture
1.5 mM (the final concentration) magnesium acetate, magnesium chloride or magnesium sulfate
0.4 μg T. th. RecA The above materials were mixed in a 1×rTaq buffer to make a total volume of 25 μl.

Reaction Solution C:
0.8 μM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 μg T. th. RecA The above materials were mixed in a 1×Taq buffer to make a total volume of 25 μl.

Reaction Solution D:
0.8 μM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 μg T. th. RecA
400 μM ATP The above materials were mixed in a 1×rTaq buffer (manufactured by Takara Bio Inc.) to make a total volume of 25 μl.

The above reaction solutions were thermally denatured at 94° C. for 30 seconds. Thereafter, the amplification reaction was carried out with 35 cycles (1 cycle: at 94° C. for 15 seconds, at 55° C. for 30 seconds and at 72° C. for 90 seconds). Thereafter, the amplification reaction was completed by the final reaction cycle at 72° C. for 3 minutes and at 4° C. for 10 minutes. After the amplification, 10 μl of the reaction solution was subjected to electrophoresis with 1.2% agarose gel. After the electrophoresis, the bands were visualized by staining the gel with ethidium bromide, and then the electrophoresis gel was photographed. Furthermore, the same experiment was conducted using Primer Sets 2, 3, 4, 5 and 6.

Results

The results are shown in FIG. 1.

Lanes 1 to 6 show the results after carrying out the amplification reaction using Primer Sets 1, 2, 3, 4, 5 and 6, respectively, without adding any of T. th. RecA and ATP in an rTaq Buffer (Reaction solution A).

Lanes 7 to 12 show the results after carrying out the amplification reaction using Primer Sets 1, 2, 3, 4, 5 and 6, respectively, with adding only T. th. RecA and without adding ATP in an rTaq Buffer (Reaction solution B).

Lanes 13 to 18 show the results after carrying out the amplification reaction using Primer Sets 1, 2, 3, 4, 5 and 6, respectively, with adding only T. th. RecA in a Taq Buffer (Reaction solution C).

Lanes 19 to 24 show the results after carrying out the amplification reaction using Primer Sets 1, 2, 3, 4, 5 and 6, respectively, with adding T. th. RecA and ATP in an rTaq Buffer (Reaction solution D).

The cases of amplification using the rTaq Buffer as the PCR reaction solution in the presence of RecA (Lanes 7 to 12) were compared with the cases of amplification using the Taq Buffer as the PCR reaction solution in the presence of RecA (Lanes 13 to 18). Non-specific amplification was observed in both of them, and particularly non-specific amplification in PCR amplification was found in the cases of Lanes 7 to 12.

That is, it was found that decrease in the performance of RecA occurred by changes in the composition of the PCR reaction solution.

In addition, the cases of PCR amplification by adding ATP and T. th. RecA (Lanes 19 to 24) were compared with the cases of PCR amplification by adding only T. th. RecA (Lanes 7 to 12) in the same PCR reaction solution. As a result, it was found that non-specific amplification can be remarkably reduced when PCR amplification was carried out in the presence of ATP and T. th. RecA.

According to the above results, it was found that the performance of T. th. RecA decreased by changes in the composition of the PCR reaction solution. It was also found that such decrease in the performance can be remarkably reduced by the presence of ATP, and only the target nucleic acid can be specifically amplified by suppressing non-specific amplification. This is considered to be due to the reason that ATP can improve the resistance of T. th. RecA to the composition of the reaction solution. Therefore, a theory is derived which states that ATP can suppress decrease in the performance of T. th. RecA due to external factors, and plays an important role in maintaining its biological activity, and its activation.

Example 2

Improvement of Decrease in the Performance of T. th. RecA in PCR

By observing the progress of the amplification cycles, improvement of decrease in the performance of T. th. RecA in PCR was confirmed by the presence of ATP.

Method

The PCR amplification reaction was carried out using a human genome DNA as a template and Primer Set 7. Two kinds of PCR reaction solution were prepared as shown below. Specifically, Reaction solution E was prepared by adding T. th. RecA only. Reaction solution F was prepared by adding ATP in addition to T. th. RecA. The composition of each of the reaction solutions is as shown below. As a DNA polymerase, an rTaq-HS polymerase was used.

Reaction Solution E:
0.8 μM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 μg T. th. RecA The above materials were mixed in a 1×Taq buffer (manufactured by Takara Bio Inc.) to make a total volume of 25 μl.

Reaction Solution F:
0.8 μM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 μg T. th. RecA
400 μM ATP The above materials were mixed in a 1×Taq buffer (manufactured by Takara Bio Inc.) to make a total volume of 25 μl.

The above reaction solutions were thermally denatured at 94° C. for 30 seconds. Thereafter, the amplification reaction was conducted in 28, 32 or 36 cycles (1 cycle: at 94° C. for 15 seconds, at 55° C. for 30 seconds and at 72° C. for 90 seconds). And Thereafter, the amplification reaction was completed by the final reaction cycle at 72° C. for 3 minutes and at 4° C. for 10 minutes. After the amplification, 10 μl of the reaction solution was subjected to electrophoresis with 1.2% agarose gel. After the electrophoresis, the bands were visualized by staining the gel with ethidium bromide, and then the electrophoresis gel was photographed. Furthermore, the same experiment was conducted using Primer Sets 8 and 9.

Results

Figure 2:
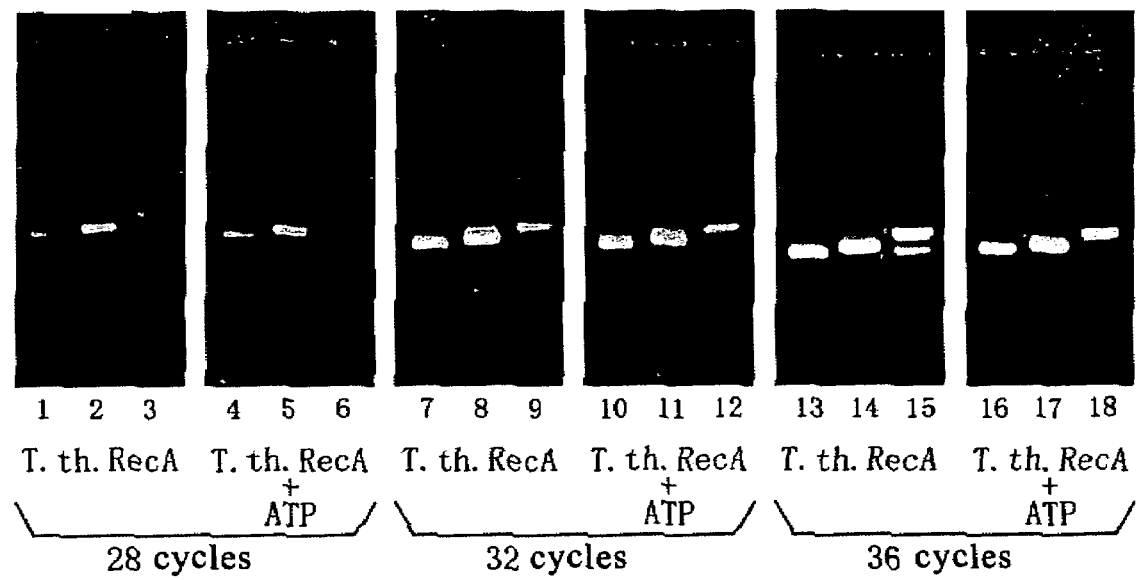
FIG. 2 is a drawing showing the results of Example 2 in which it was confirmed that the method of the present invention improved the decrease in performance of T. th. RecA in PCR.

The results are shown in FIG. 2.

Lanes 1 to 3 show the results after carrying out the amplification reaction for 28 cycles by Primer Sets 7, 8 and 9, respectively, without adding ATP and with adding only T. th. RecA (Reaction solution E).

Lanes 4 to 6 show the results after carrying out the amplification reaction for 28 cycles by Primer Sets 7, 8 and 9, respectively, with adding T. th. RecA and ATP (Reaction solution F).

Lanes 7 to 9 show the results after carrying out the amplification reaction for 32 cycles by Primer Sets 7, 8 and 9, respectively, without adding ATP and with adding only T. th. RecA (Reaction solution E).

Lanes 10 to 12 show the results after carrying out the amplification reaction for 32 cycles by Primer Sets 7, 8 and 9, respectively, with adding T. th. RecA and ATP (Reaction solution F).

Lanes 13 to 15 show the results after carrying out the amplification reaction for 36 cycles by Primer Sets 7, 8 and 9, respectively, without adding ATP and with adding only T. th. RecA (Reaction solution E).

Lanes 16 to 18 show the results after carrying out the amplification reaction for 36 cycles by Primer Sets 7, 8 and 9, respectively, with adding T. th. RecA and ATP (Reaction solution F).

When PCR amplification was carried out by adding only T. th. RecA, it was found that non-specific amplification products were formed every time the cycle number increased (comparison of Lanes 1 to 3 and Lanes 7 to 9 with Lanes 13 to 15).

On the other hand, it was found that such non-specific amplification can be suppressed by adding ATP (comparison of Lanes 1 to 3 with Lanes 4 to 6, comparison of Lanes 7 to 9 with Lanes 10 to 12, and comparison of Lanes 13 to 15 with Lanes 16 to 18). Also, it was found that such non-specific amplification can be suppressed effectively even when the cycle number increased (Comparison of Lanes 4 to 6 and Lanes 10 to 12 with Lanes 16 to 18).

According to the above results, it was found that the performance of T. th. RecA decreases with the increase of the cycle number due to thermal denaturation, etc. during PCR. However, it was also found that such performance decrease can be suppressed effectively by adding ATP. Further, it was found that, by carrying out PCR amplification in the presence of T. th. RecA and ATP, it was possible to amplify only the target nucleic acid specifically by suppressing non-specific amplification. It is considered that ATP can improve the stability of the biological function of T. th. RecA against external factors, especially to heat, such as the thermostability. Therefore, a theory is derived also from this which states that ATP plays an important role in activating T. th. RecA and maintaining its biological function in the PCR cycles. In addition, it was also found that, by carrying out PCR amplification in the presence of T. th. RecA and ATP, it was possible to reduce consumption of dNTP added to the reaction system, and to suppress decrease in the performance of T. th. RecA.

Example 3

Effects on the Amplification with an Ex Taq Polymerase

It was confirmed that amplification using T. th. RecA and ATP had the effects of reducing non-specific amplification also in the amplification with an Ex Taq polymerase.

Method

The PCR amplification reaction was carried out using a human genome DNA as a template and Primer Set 1. Two kinds of PCR reaction solutions were prepared as shown below. Specifically, Reaction solution G was prepared with a composition of a general PCR reaction solution without adding any of T. th. RecA and ATP (Control). Reaction solution H was prepared by adding T. th. RecA and ATP further to Reaction solution G. The composition of each of the reaction solutions is as shown below. As a DNA polymerase, an Ex Taq-HS polymerase was used.

Reaction Solution G (Control):

0.8 μM (the final concentration) Primer set 25 ng Template DNA 0.7 unit DNA polymerase 0.2 mM (the final concentration) dNTP mixture 1.5 mM (the final concentration) magnesium acetate, magnesium chloride or magnesium sulfate The above materials were mixed in a 1×Taq buffer (manufactured by Takara Bio Inc.) to make a total volume of 25 μl.

Reaction Solution H:

0.8 μM (the final concentration) Primer set 25 ng Template DNA 0.7 unit DNA polymerase 0.2 mM (the final concentration) dNTP mixture 1.5 mM (the final concentration) magnesium acetate, magnesium chloride or magnesium sulfate 0.4 μg T. th. RecA 400 μM ATP The above materials were mixed in a 1×Taq buffer (manufactured by Takara Bio Inc.) to make a total volume of 25 μl.

The above reaction solutions were thermally denatured at 94° C. for 30 seconds. Thereafter, the amplification reaction was carried out with 36 cycles (1 cycle: at 94° C. for 15 seconds, at 55° C. for 30 seconds and at 72° C. for 90 seconds). Thereafter, the amplification reaction was completed by the final reaction cycle at 72° C. for 3 minutes and at 4° C. for 10 minutes. After the amplification, 10 μl of the reaction solution was subjected to electrophoresis with 1.2% agarose gel. After the electrophoresis, the bands were visualized by staining the gel with ethidium bromide, and then the electrophoresis gel was photographed. Furthermore, the same experiment was conducted using Primer Sets 2, 3, 4, 5, 6 and 8.

Results

Figure 3:
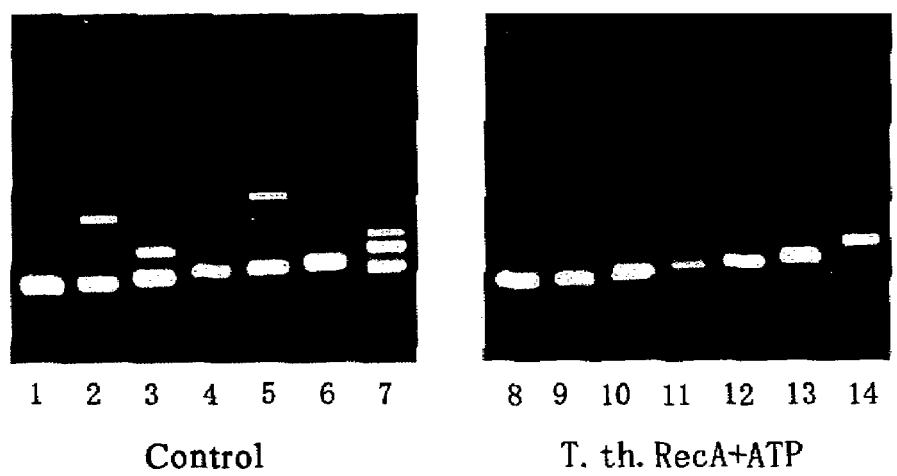
FIG. 3 is a drawing showing the results of Example 3 in which effects of the method of the present invention on amplification with an Ex Taq polymerase were investigated.

The results are shown in FIG. 3.

Lanes 1 to 7 show the results after carrying out the amplification reaction in the general PCR reaction solution using Primer Sets 1, 2, 3, 4, 5, 6 and 8, respectively, without adding any of T. th. RecA and ATP (Control: Reaction solution G).

Lanes 8 to 14 show the results after carrying out the amplification reaction using Primer Sets 1, 2, 3, 4, 5, 6 and 8, respectively, by adding T. th. RecA and ATP (Reaction solution H).

In amplification with the Ex Taq polymerase, non-specific amplification was suppressed also by adding ATP to T. th. RecA (comparison of Lanes 1 to 7 with Lanes 8 to 14).

According to the above results, it was found that, regardless of the kind of the DNA polymerase, non-specific amplification of the DNA polymerase can be suppressed and the target nucleic acid was amplified specifically by adding T. th. RecA and ATP.

Example 4

Confirmation of Effects by Various Nucleotide 5'-triphosphates

It was confirmed that stabilization of T. th. RecA is achieved by various nucleotide 5'-triphosphates as in the case of ATP by carrying out PCR amplification in the presence of various nucleotide 5'-triphosphates and T. th. RecA.

Method

The PCR amplification reaction was carried out using a human genome DNA as a template and Primer Set 1. Seven kinds of PCR reaction solution were prepared as shown below. Specifically, Reaction solution I was a general PCR reaction solution and prepared without adding any of T. th. RecA and nucleotide 5'-triphosphate (Control). Reaction solution J was prepared by adding T. th. RecA to Reaction solution I. Reaction solutions K, L, M and N were prepared by adding GTP, ATP, UTP and CTP to Reaction solution J, respectively. Reaction solution O was prepared by adding only ATP to Reaction solution I without adding T. th. RecA. The composition of each of the reaction solutions is as shown below. As a DNA polymerase, an rTaq-HS polymerase was used.

Reaction Solution I (Control):
0.8 µM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
The above was mixed in an rTaq Buffer to make a total volume of 25 µl.

Reaction Solution J:
0.8 µM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 µg T. th. RecA
The above materials were mixed in a 1×rTaq buffer (manufactured by Takara Bio Inc.) to make a total volume of 25 µl.

Reaction Solution K:
0.8 µM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 µg T. th. RecA
400 µM GTP
The above materials were mixed in a 1×rTaq buffer (manufactured by Takara Bio Inc.) to make a total volume of 25 µl.

Reaction Solution L:
0.8 µM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 µg T. th. RecA
400 µM ATP
The above materials were mixed in a 1×rTaq buffer (manufactured by Takara Bio Inc.) to make a total volume of 25 µl.

Reaction Solution M:
0.8 µM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 µg T. th. RecA
400 µM UTP
The above materials were mixed in a 1×rTaq buffer (manufactured by Takara Bio Inc.) to make a total volume of 25 µl.

Reaction Solution N:
0.8 µM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
0.4 µg T. th. RecA
400 µM CTP
The above materials were mixed in a 1×rTaq buffer (manufactured by Takara Bio Inc.) to make a total volume of 25 µl.

Reaction Solution O:
0.8 µM (the final concentration) Primer set
25 ng Template DNA
0.7 unit DNA polymerase
0.2 mM (the final concentration) dNTP mixture
1.5 mM (the final concentration) magnesium acetate, magnesium chloride or magnesium sulfate
400 µM ATP
The above materials were mixed in a 1×rTaq buffer (manufactured by Takara Bio Inc.) to make a total volume of 25 µl.

The above reaction solutions were thermally denatured at 94° C. for 30 seconds. Thereafter, the amplification reaction was carried out with 36 cycles (1 cycle: at 94° C. for 15 seconds, at 55° C. for 30 seconds and at 72° C. for 90 seconds). Thereafter, the amplification reaction was completed by the final reaction cycle at 72° C. for 3 minutes and at 4° C. for 10 minutes. After the amplification, 10 µl of the reaction solution was subjected to electrophoresis with 1.2% agarose gel. After the electrophoresis, the bands were visualized by staining the gel with ethidium bromide, and then the electrophoresis gel was photographed. Furthermore, the same experiment was conducted using Primer Sets 2, 3, 4, 5, 6 and 8.

Results

Figure 4:
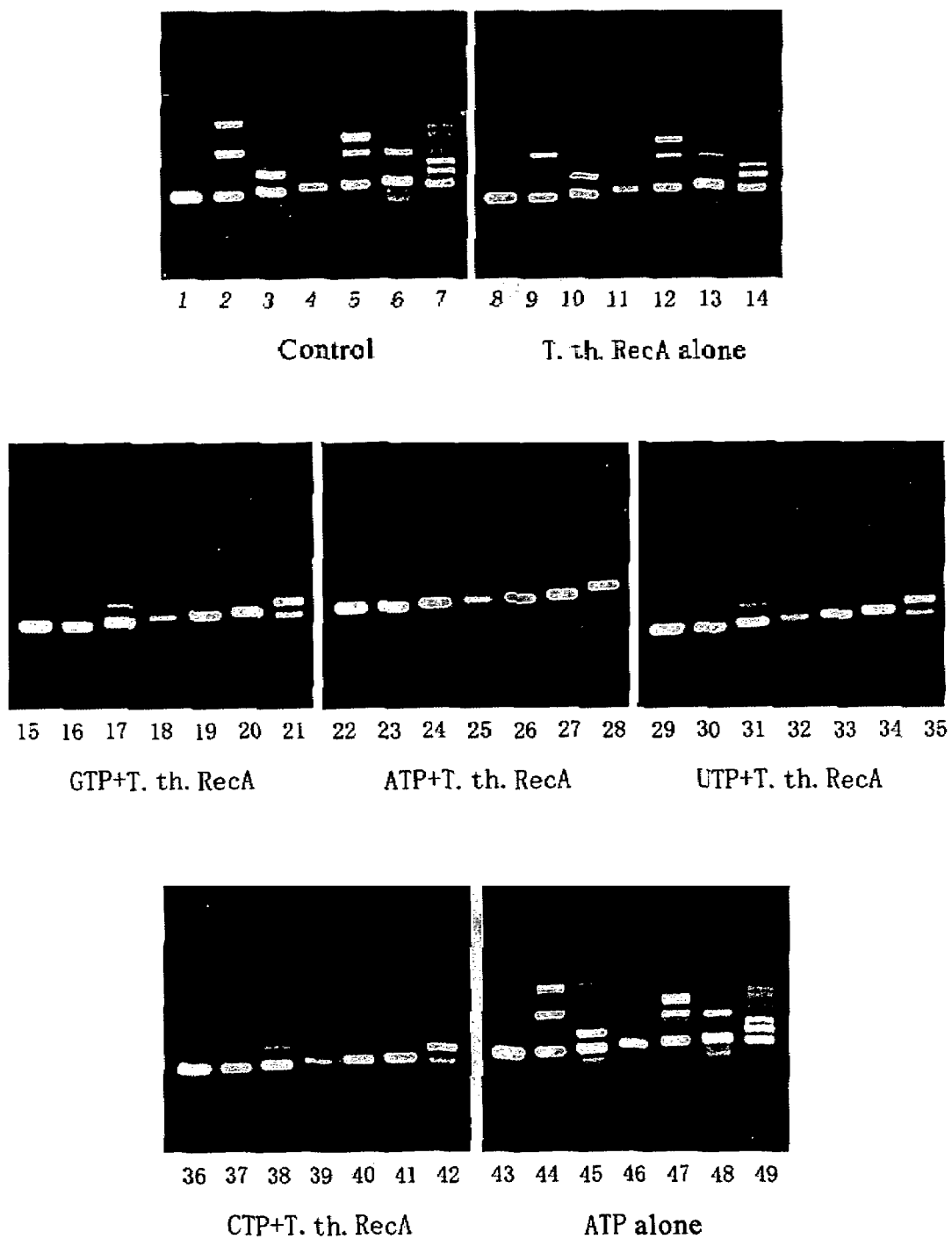
FIG. 4 is a drawing showing the results of Example 4 in which effects of various nucleotide 5'-triphosphates and T. th. RecA on PCR amplification were investigated.

The results are shown in FIG. 4.

Lanes 1 to 7 show the results after carrying out the amplification reaction in the general PCR reaction solution using Primer Sets 1, 2, 3, 4, 5, 6 and 8, respectively, without adding any of T. th. RecA and NTP (Control: Reaction solution I).

Lanes 8 to 14 show the results after carrying out the amplification reaction using Primer Sets 1, 2, 3, 4, 5, 6 and 8, respectively, by adding only T. th. RecA and without adding any NTP (Reaction solution J).

Lanes 15 to 21 show the results after carrying out the amplification reaction using Primer Sets 1, 2, 3, 4, 5, 6 and 8, respectively, by adding T. th. RecA and GTP (Reaction solution K).

Lanes 22 to 28 show the results after carrying out the amplification reaction using Primer Sets 1, 2, 3, 4, 5, 6 and 8, respectively, by adding T. th. RecA and ATP (Reaction solution L).

Lanes 29 to 35 show the results after carrying out the amplification reaction using Primer Sets 1, 2, 3, 4, 5, 6 and 8, respectively, by adding T. th. RecA and UTP (Reaction solution M).

Lanes 36 to 42 show the results after carrying out the amplification reaction using Primer Sets 1, 2, 3, 4, 5, 6 and 8, respectively, by adding T. th. RecA and CTP (Reaction solution N).

Lanes 43 to 49 show the results after carrying out the amplification reaction using Primer Sets 1, 2, 3, 4, 5, 6 and 8, respectively, by adding only ATP and without adding T. th. RecA (Reaction solution O).

It was found that non-specific amplification can be suppressed when T. th. RecA and ATP were added to the PCR system compared to the case where only T. th. RecA was added (comparison of Lanes 15 to 21 with Lanes 8 to 14). These results confirmed the results of Examples 1 to 3.

In addition, similar results were found also in the case where GTP and T. th. RecA were added (comparison of Lanes 15 to 21 with Lanes 8 to 14), in the case where UTP and T. th. RecA were added (comparison of Lanes 29 to 35 with Lanes 8 to 14), and in the case where CTP and T. th. RecA were added (comparison of Lanes 36 to 42 with Lanes 8 to 14).

Among these, it was found that the combination of ATP and T. th. RecA suppressed non-specific amplification the most.

However, with ATP alone, non-specific amplification was not suppressed (Lanes 43 to 49). And with ATP alone, production of non-specific amplification products was found to be of the same degree as in the case where any of T. th. RecA and ATP were added (comparison of Lanes 43 to 49 with Lanes 1 to 7).

According to the above results, it was found that non-specific amplification can be suppressed by carrying out the PCR amplification reaction in the presence of T. th. RecA and nucleotide 5'-triphosphate such as GTP, CTP and UTP as well as ATP. As a result, it is possible to amplify only the target nucleic acid specifically, which increases amplification efficiency. On the other hand, such effects were not confirmed with nucleotide 5'-triphosphate alone.

Therefore, it was found that nucleotide 5'-triphosphate such as GTP, CTP and UTP as well as ATP can activate T. th. RecA, and that it plays an important role in stabilizing the functions of T. th. RecA. It is considered that the stability of the biological function of RecA against external factors, especially to heat, can be improved and the biological function of RecA can be activated.

Example 5

Effects of the Length of Primer: 1

Effects of the base-length of the primer to be used on PCR amplification in the presence of T. th. RecA and ATP were investigated.

Method

The PCR amplification reaction was carried out using a human genome DNA as a template and the primer sets of various lengths. The primer sets used here were Primer Sets 10, 11, 12, 13, 14 and 15 with the base length of 20, 25, 30, 35, 40 and 45, respectively. Two kinds of PCR reaction solution were prepared as shown below. Specifically, Reaction solution P was prepared by adding T. th. RecA and ATP. Reaction solution Q was prepared similarly to Reaction solution P except that ATP was not added. The composition of each of the reaction solutions was as shown below. As a DNA polymerase, an ExTaq-HS polymerase (manufactured by Takara Bio Inc.) was used.

Reaction Solution P:
0.6 µM (the final concentration) Primer set
20 ng Template DNA
0.7 unit DNA polymerase
0.2 mM (the final concentration) dNTP mixture
1.5 mM (the final concentration) magnesium acetate, magnesium chloride or magnesium sulfate
0.4 µg T. th. RecA
0.4 mM (the final concentration) ATP The above materials were mixed in a 1×ExTaq buffer to make a total volume of 25 µl.

Reaction Solution Q:
0.6 µM (the final concentration) Primer set
20 ng Template DNA
0.7 unit DNA polymerase
0.4 mM (the final concentration) dNTP mixture
1.5 mM (the final concentration) magnesium acetate, magnesium chloride or magnesium sulfate
0.4 µg T. th. RecA
The above materials were mixed in a 1×ExTaq buffer to make a total volume of 25 µl.

The above reaction solutions were thermally denatured at 94° C. for 30 seconds. Thereafter, the amplification reaction was carried out with 35 cycles (1 cycle: at 94° C. for 15 seconds, at 55° C. for 30 seconds and at 72° C. for 90 seconds). Thereafter, the amplification reaction was completed by the final reaction cycle at 72° C. for 3 minutes and at 4° C. for 10 minutes. After the amplification, 10 µl of the reaction solution was subjected to electrophoresis with 1.2% agarose gel. After the electrophoresis, the bands were visualized by staining the gel with ethidium bromide, and then the electrophoresis gel was photographed.

Results

Figure 5:
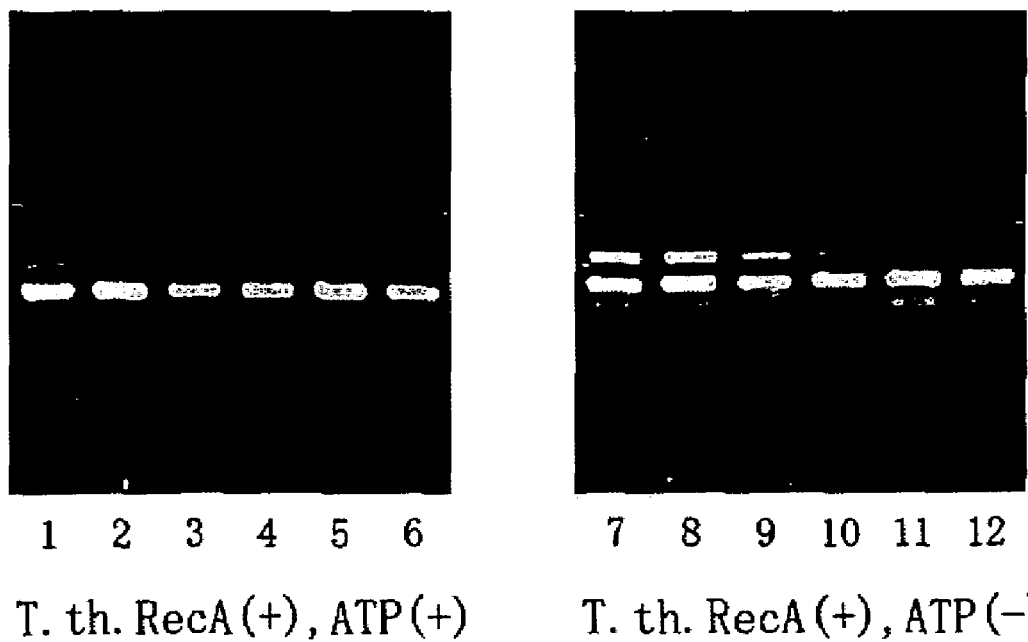
FIG. 5 is a drawing showing the results of Example 5 in which effects of the primer length were investigated.

The results are shown in FIG. 5.

Lanes 1 to 6 show the results after carrying out the amplification reaction using Primer Sets 10, 11, 12, 13, 14 and 15, respectively, by adding T. th. RecA and ATP (Reaction solution P).

Lanes 7 to 12 show the results after carrying out the amplification reaction using Primer Sets 10, 11, 12, 13, 14 and 15, respectively, without adding ATP and by adding only T. th. RecA (Reaction solution Q).

In the case of PCR amplification in the presence of both of T. th. RecA and ATP, it was found that non-specific amplification can be remarkably reduced and the template nucleic acid can be specifically amplified with any primer set in PCR amplification (Lanes 1 to 6). The various primer sets used here have different base-lengths of 20 to 45, respectively. Therefore, it was found that specific amplification of the target nucleic acid can be achieved in the presence of T. th. RecA and ATP, regardless of the primer length. On the other hand, it was found that non-specific amplification products were produced in the case of amplification without adding ATP and with adding only T. th. RecA (Lanes 7 to 12).

The above results conform to the results of Examples 1 to 4 in which formation of non-specific amplification products is suppressed by T. th. RecA and ATP and PCR amplification efficiency was improved. Therefore, it was found that the effects of T. th. RecA and ATP on improving the amplification efficiency for the target nucleic acid is not affected by the length of the primer set. Therefore, it was found that the present invention can be used in any PCR amplification reaction without limitation to the length of the primer set to be used.

Example 6

Effects of the Length of Primer: 2

In continuation of Example 5, effects of the base-length of the primer to be used on PCR amplification in the presence of T. th. RecA and ATP were investigated.

Method

The PCR amplification reaction was carried out using a human genome DNA as a template and the primer sets of various lengths. The primer sets used here were Primer Sets 16, 17, 18, 19, 20 and 21 with the base lengths of 20, 25, 30, 35, 40 and 45. The same PCR reaction solutions as in Example 5 were used. Specifically, Reaction solution P was prepared by adding T. th. RecA and ATP. Reaction solution Q was prepared similarly to Reaction solution P except that ATP was not added. As a DNA polymerase, an ExTaq-HS polymerase (manufactured by Takara Bio Inc.) was used. Then, the PCR reaction was carried out under the same conditions as in Example 5, then electrophoresis and staining of the electrophoresed gel were conducted, and then photographing was conducted according to the same procedures as in Example 5.

Results

Figure 6:
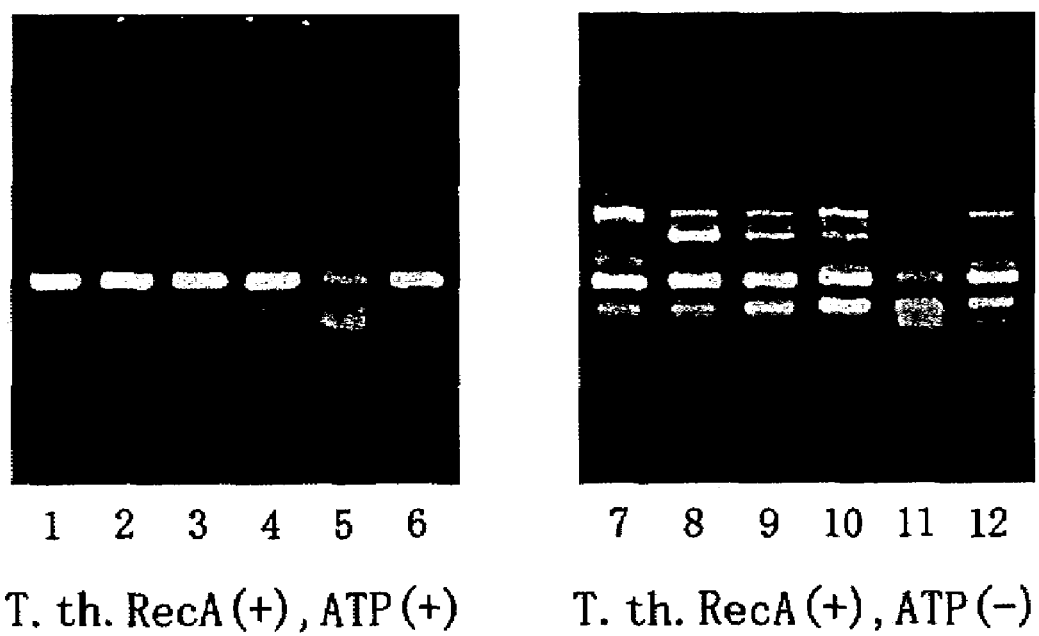
FIG. 6 is a drawing showing the results of Example 6 in which effects of the primer length were investigated.

The results are shown in FIG. 6.

Lanes 1 to 6 show the results after carrying out the amplification reaction using Primer Sets 16, 17, 18, 19, 20 and 21, respectively, with adding T. th. RecA and ATP (Reaction solution P).

Lanes 7 to 12 show the results after carrying out the amplification reaction using Primer Sets 16, 17, 18, 19, 20 and 21, respectively, with adding only T. th. RecA (Reaction solution Q).

In the case of amplification in the presence of both of T. th. RecA and ATP, it was found that non-specific amplification was remarkably suppressed and specific amplification of the template nucleic acid was achieved with any primer set in PCR amplification (Lanes 1 to 6). The various primer sets used here have different base-length of 20 to 45, respectively. That is, it was found that specific amplification can be achieved by RecA and ATP, regardless of. the primer length. On the other hand, non-specific amplification was found in the case of amplification in the presence of only RecA without adding ATP (Lanes 7 to 12)

The above results conformed to the results of Example 5. It was confirmed that, in the PCR reaction, the effects of improving amplification efficiency for the target nucleic acid by T. th. RecA and ATP are not affected by the length of the primer set.

Example 7

Effects of Combination with a T. th. DNA Polymerase

Effects of combination of T. th. RecA with ATP on PCR amplification using a T. th. DNA polymerase were investigated.

Method

PCR amplification by the T. th. DNA polymerase was carried out using a human genome DNA as a template and Primer Set 1. Five kinds of PCR reaction solution were prepared as shown below. Specifically, Reaction solution R was prepared by adding T. th. RecA and ATP. Reaction solution S was prepared similarly to Reaction solution R except that ATP was not added. Reaction solution T was prepared similarly to Reaction solution R except that ATP and T. th. RecA were not added, and had a composition of a general PCR reaction solution. Reaction solution U was prepared similarly to Reaction solution R except that T. th. RecA and ATP were not added but a T. th. RecA storage buffer was added instead. Further, Reaction solution V was prepared similarly to Reaction solution R except that T. th. RecA was not added. The composition of each of the reaction solutions is as shown below.

Reaction Solution R:
0.6 µM (the final concentration) Primer set
20 ng Template DNA
0.5 unit DNA polymerase
0.2 mM (the final concentration) dNTP mixture
1.5 mM (the final concentration) magnesium acetate, magnesium chloride or magnesium sulfate
0.4 µg T. th. RecA
0.4 mM (the final concentration) ATP The above materials were mixed in a 1×T. th. DNA polymerase buffer (manufactured by Applied Biosystems) to make a total volume of 25 µl.

Reaction Solution S:
0.6 µM (the final concentration) Primer set
20 ng Template DNA
0.5 unit DNA polymerase
0.2 mM (the final concentration) dNTP mixture
1.5 mM (the final concentration) magnesium acetate, magnesium chloride or magnesium sulfate
0.4 µg T. th. RecA The above materials were mixed in a 1×T. th. DNA polymerase buffer (manufactured by Applied Biosystems) to make a total volume of 25 µl.

Reaction Solution T:
0.6 µM (the final concentration) Primer set
20 ng Template DNA
0.5 unit DNA polymerase
0.2 mM (the final concentration) dNTP mixture
1.5 mM (the final concentration) magnesium acetate, magnesium chloride or magnesium sulfate The above materials were mixed in a 1×T. th. DNA polymerase buffer (manufactured by Applied Biosystems) to make a total volume of 25 µl.

Reaction Solution U:
0.6 µM (the final concentration) Primer set
20 ng Template DNA
0.5 unit DNA polymerase
0.2 mM (the final concentration) dNTP mixture
1.5 mM (the final concentration) magnesium acetate, magnesium chloride or magnesium sulfate
0.1 µl T. th. RecA storage buffer The above materials were mixed in a 1×T. th. DNA polymerase buffer (manufactured by Applied Biosystems) to make a total volume of 25 µl.

The composition of T. th. RecA storage buffer used herein is as shown below.
1.5 M KCl
50 mM Tris-HCl (pH 7.5)
1.0 mM EDTA
0.5 mM DTT
50% glycerol Reaction Solution V:
0.6 µM (the final concentration) Primer set
20 ng Template DNA
0.5 unit DNA polymerase
0.2 mM (the final concentration) dNTP mixture
1.5 mM (the final concentration) magnesium acetate, magnesium chloride or magnesium sulfate
0.4 mM (the final concentration) ATP The above materials were mixed in a 1×T. th. DNA polymerase buffer (manufactured by Applied Biosystems) to make a total volume of 25 μl.

The above reaction solutions were thermally denatured at 92° C. for 30 seconds. Then, amplification reaction was carried out with 35 cycles (1 cycle: at 94° C. for 15 seconds, at 55° C. for 30 seconds and at 68° C. for 90 seconds). Thereafter, the amplification reaction was completed by the final reaction cycle at 68° C. for 3 minutes and at 4° C. for 10 minutes. After the amplification, 10 μl of the reaction solution was subjected to electrophoresis with 1.2% agarose gel. After the electrophoresis, the bands were visualized by staining the gel with ethidium bromide, and then the electrophoresis gel was photographed. Furthermore, the same amplification reaction was conducted using Primer Sets 2, 3, 4, 5, 6 and 8.

Results

Figure 7:
FIG. 7 is a drawing showing the results of Example 7 in which effects of combination with a T. th. DNA polymerase were investigated.
Figure 7:
Figure 7:
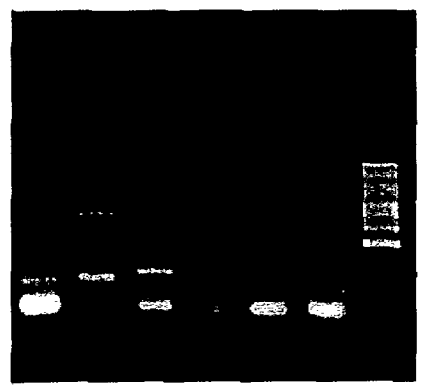
Figure 7:
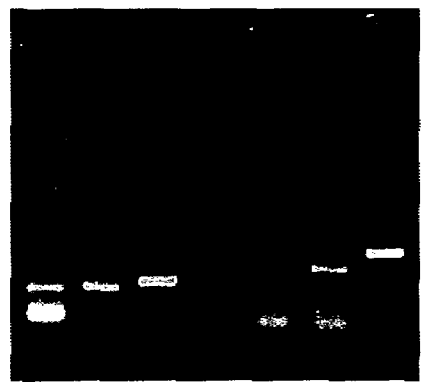
Figure 7:

The results are shown in FIG. 7.

Every one shows the results after carrying out PCR amplification by the T. th. DNA polymerase.

Lanes 1 to 7 show the results after carrying out the amplification reaction using Primer Sets 1, 2, 3, 4, 5, 6 and 8, respectively, by adding T. th. RecA and ATP (Reaction solution R).

Lanes 8 to 14 show the results after carrying out the amplification reaction using Primer Sets 1, 2, 3, 4, 5, 6 and 8, respectively, without adding ATP and by adding T. th. RecA (Reaction solution S).

Lanes 15 to 21 show the results after carrying out the amplification reaction using Primer Sets 1, 2, 3, 4, 5, 6 and 8, respectively, without adding any of T. th. RecA and ATP (Reaction solution T).

Lanes 22 to 28 show the results after carrying out the amplification reaction using Primer Sets 1, 2, 3, 4, 5, 6 and 8, respectively, without adding any of T. th. RecA and ATP but with adding a T. th. RecA storage buffer (Reaction solution U).

Lanes 29 to 35 show the results after carrying out the amplification reaction using Primer Sets 1, 2, 3, 4, 5, 6 and 8, respectively, without adding T. th. RecA but with adding ATP only (Reaction solution V).

In the case of amplification with the T. th. DNA polymerase in the presence of both of T. th. RecA and ATP, it was found that non-specific amplification was remarkably suppressed and the template nucleic acid was specifically amplified (Lanes 1 to 7). On the other hand, production of non-specific amplification products was found in the case of amplification without any addition (Lanes 8 to 14), in the case of amplification only with T. th. RecA (Lanes 15 to 21), or in the case of amplification only with ATP (Lanes 22 to 28 and Lanes 29 to 35).

The above results confirmed that the effects of improving amplification efficiency by T. th. RecA and ATP are achieved also in amplification by the T. th. DNA polymerase, similarly to the results of Examples 1 to 6. Furthermore, it was found that the effects were more remarkably achieved in amplification by the T. th. DNA polymerase compared to the results of Examples 1 to 6 in which the Taq DNA polymerase was used. Therefore, the present invention is not limited in its use to the kinds of the DNA polymerase used in PCR amplification. In addition, particularly, it was found that the present invention can be suitably used in the PCR amplification reaction by the T. th. DNA polymerase.

Example 8

Effects of Multiplex PCR by Combination with the T. th. DNA Polymerase

Effects of combination of T. th. RecA with ATP on PCR amplification using the T. th. DNA polymerase, and effects on multiplex PCR were investigated.

Method

The PCR amplification reaction by the T. th. DNA polymerase was carried out using a human genome DNA as a template. The primer sets used herein were Primer Sets 22, 23, 24, 25, 26, 27, 28, 29, 30, 31, 32, 33, 1 and 2. In addition, multiplex PCR was carried out in which these primer sets were added in one reaction system and amplified. Two kinds of PCR reaction solution were prepared as shown below. Specifically, Reaction solution W was prepared by adding T. th. RecA and ATP. Reaction solution X was prepared similarly to Reaction solution W except that T. th. RecA and ATP were not added but a T. th. RecA storage buffer was added instead.

Reaction Solution W:

0.6 μM (the final concentration) Primer set 20 ng Template DNA 0.5 unit DNA polymerase 0.2 mM (the final concentration) dNTP mixture 1.5 mM (the final concentration) magnesium acetate, magnesium chloride or magnesium sulfate 0.4 μg T. th. RecA 0.4 mM (the final concentration) ATP The above materials were mixed in a 1×T. th. DNA polymerase buffer (manufactured by Applied Biosystems) to make a total volume of 25 μl.

Reaction Solution X:

0.6 μM (the final concentration) Primer set 20 ng Template DNA 0.5 unit DNA polymerase 0.2 mM (the final concentration) dNTP mixture 1.5 mM (the final concentration) magnesium acetate 0.1 μl T. th. RecA storage buffer The above materials were mixed in a 1×T. th. DNA polymerase buffer (Product No. N8080187, manufactured by Applied Biosystems) to make a total volume of 25 μl. The T. th. RecA storage buffer used here was the same as used in Example 7.

The above reaction solutions were thermally denatured at 92° C. for 30 seconds. Thereafter, the amplification reaction was carried out with 35 cycles (1 cycle: at 94° C. for 15 seconds, at 55° C. for 30 seconds and at 68° C. for 2 minutes). Thereafter, the amplification reaction was completed by the final reaction cycle at 68° C. for 3 minutes and at 4° C. for 10 minutes. After the amplification, 3 μl of the reaction solution was subjected to electrophoresis with 12.5% acrylamide gel. After the electrophoresis, the bands were visualized by staining the gel with cyber green, and then the electrophoresis gel was photographed.

Results

Figure 8:
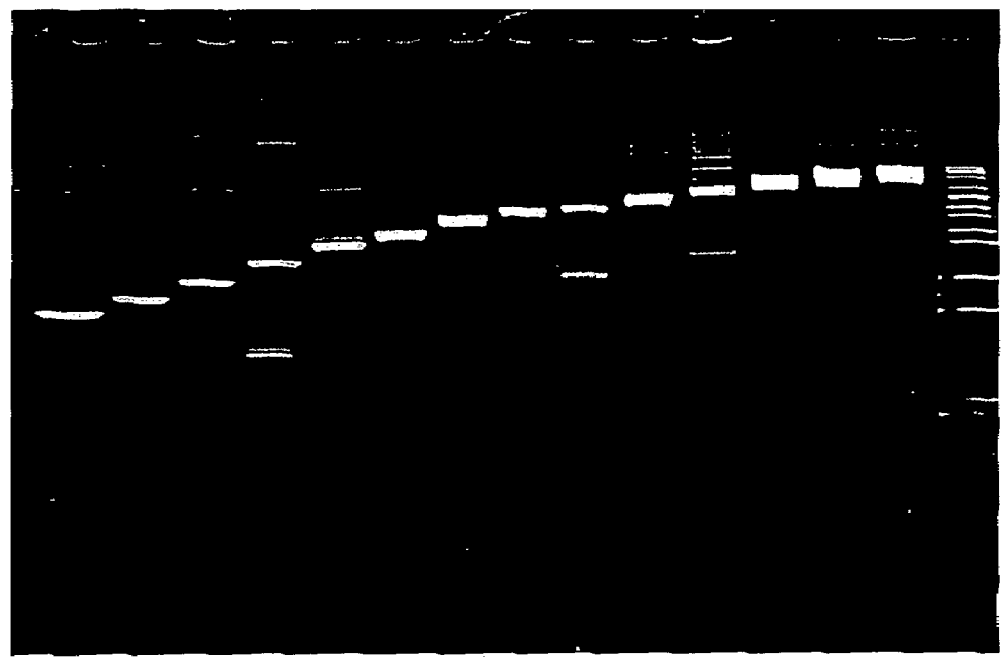
FIG. 8 is a drawing showing the results of Example 8 in which effects of combination with a T. th. DNA polymerase by multiplex PCR were investigated.
Figure 8:
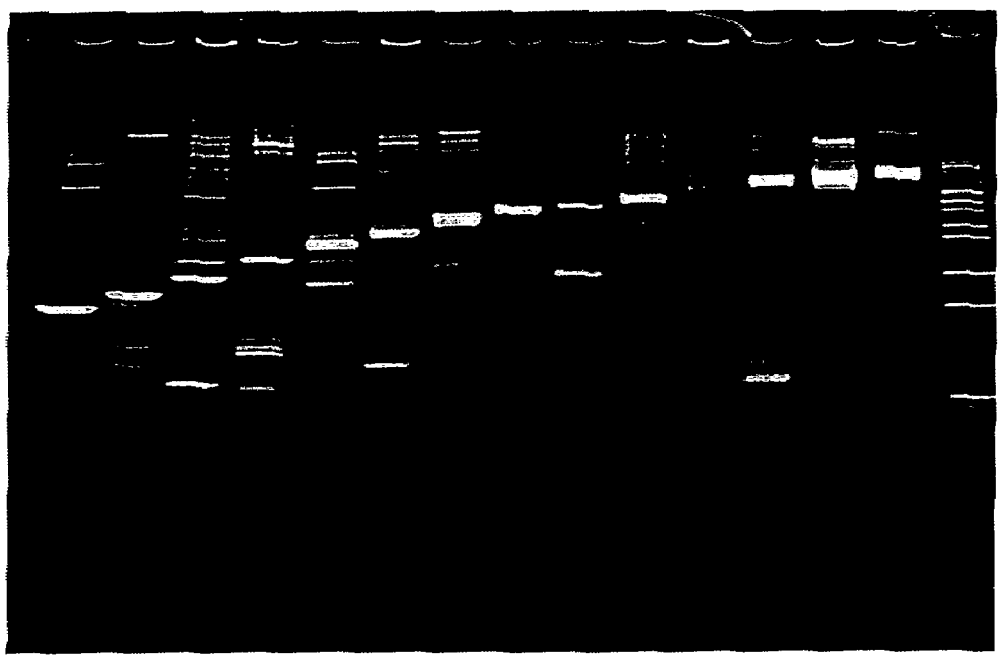

The results are shown in FIG. 8.

Every one shows the results after carrying out PCR amplification by the T. th. DNA polymerase.

Lanes 1 to 14 show the results after carrying out the amplification reaction using Primer Sets 22, 23, 24, 25, 26, 27, 28, 29, 30, 31, 32, 33, 1 and 2, respectively, by adding T. th. RecA and ATP (Reaction solution W).

Lane 15 show the results of multiplex PCR in which the amplification reaction was carried out in one reaction system by adding all of the above-mentioned primer sets in the presence of T. th. RecA and ATP (Reaction solution W).

Lanes 16 to 29 show the results after carrying out the amplification reaction using Primer Sets 22, 23, 24, 25, 26, 27, 28, 29, 30, 31, 32, 33, 1 and 2, respectively, in the presence of T. th. RecA storage buffer (Reaction solution X).

Lane 30 show the results of multiplex PCR in which the amplification reaction was carried out in one reaction system by adding all of the above-mentioned primer sets in the presence of T. th. RecA storage buffer (Reaction solution X).

In the case of carrying out amplification with the T. th. DNA polymerase in the presence of both of T. th. RecA and ATP, it was found that non-specific amplification was remarkably suppressed and the template nucleic acid was specifically amplified (Lanes 1 to 14). On the other hand, production of non-specific amplification products was found in the absence of T. th. RecA and ATP (Lanes 16 to 29).

In addition, when multiplex PCR was carried out in the presence of both of T. th. RecA and ATP, it was found that the target sequences corresponding to each of the primer sets were specifically amplified (Lane 15, for the corresponding target sequences, Lanes 1 to 14). On the other hand, in the absence of T. th. RecA and ATP, it was confirmed that production of non-specific amplification products was not suppressed, and accuracy of multiplex PCR was reduced (Lane 30).

The above results confirmed that the effects of improving amplification efficiency by T. th. RecA and ATP are achieved also in the amplification using the T. th. DNA polymerase, similarly to the results of Example 7. Furthermore, the results also confirmed that the effects were more remarkably achieved in the case of amplification using the T. th. DNA polymerase compared to the results of Examples 1 to 6 in which the Taq DNA polymerase was used. Further, from the results of the present experiment, it was found also in multiplex PCR that specific amplification of the target sequences corresponding to each of the primer sets was possible, and reliability of multiplex PCR was improved. It is considered that mis-priming between primers can be suppressed by the presence of T. th. RecA and ATP. Therefore, it is considered that mis-priming can be effectively suppressed and specific amplification of the target sequences can be performed in multiplex PCR in which a plurality of primer sets are reacted in one reaction system. Thus, it was found that the invention can be particularly suitably applied to multiplex PCR.

The present invention provides a nucleic acid amplification method which is useful in the medical field, the biochemical field, the environmental field, the food field and the like.

What is claimed is:

1. A method for amplifying a nucleic acid comprising:

performing in the presence of an activated *Thermus thermophilus* RecA protein a polymerase chain reaction that comprises multiple cycles where each cycle encompasses steps conducted at different temperatures;

wherein said activated RecA protein has been activated by the addition at least one nucleotide 5'-triphosphate with the exception of a deoxynucleotide 5'-triphosphate or a nucleotide 5'-O-thiotriphosphate;

wherein the activated RecA protein maintains its activity throughout each polymerase chain reaction cycle, and wherein said activated RecA protein has been activated by the addition of at least one hydrolyzable nucleotide 5'-triphosphate selected from the group consisting of ATP, CTP, GTP and UTP.

2. A method for amplifying a nucleic acid comprising:

performing in the presence of an activated *Thermus thermophilus* RecA protein a polymerase chain reaction that comprises multiple cycles where each cycle encompasses steps conducted at different temperatures;

wherein said activated RecA protein has been activated by the addition at least one nucleotide 5'-triphosphate with the exception of a deoxynucleotide 5'-triphosphate or a nucleotide 5'-O-thiotriphosphate;

wherein the activated RecA protein maintains its activity throughout each polymerase chain reaction cycle, and wherein said activated RecA protein has been activated by the addition of ATP as the at least one hydrolyzable nucleotide 5'-triphosphate.

* * * * *

SEQUENCE LISTING

```
<160> NUMBER OF SEQ ID NOS: 66

<210> SEQ ID NO 1
<211> LENGTH: 19
<212> TYPE: DNA
<213> ORGANISM: homo sapiens

<400> SEQUENCE: 1
acaatgggct cactcaccc                                              19

<210> SEQ ID NO 2
<211> LENGTH: 20
<212> TYPE: DNA
<213> ORGANISM: homo sapiens

<400> SEQUENCE: 2
ctaagaccaa tggatagctg                                             20

<210> SEQ ID NO 3
<211> LENGTH: 22
<212> TYPE: DNA
<213> ORGANISM: homo sapiens

<400> SEQUENCE: 3
gctcagcatg gtggtggcat aa                                          22

<210> SEQ ID NO 4
<211> LENGTH: 22
<212> TYPE: DNA
<213> ORGANISM: homo sapiens

<400> SEQUENCE: 4
cctcatacct tcccccccat tt                                          22

<210> SEQ ID NO 5
<211> LENGTH: 25
```

```
<212> TYPE: DNA
<213> ORGANISM: homo sapiens

<400> SEQUENCE: 5
gactactcta gcgactgtcc atctc                                          25

<210> SEQ ID NO 6
<211> LENGTH: 20
<212> TYPE: DNA
<213> ORGANISM: homo sapiens

<400> SEQUENCE: 6
gacagccacc agatccaatc                                                20

<210> SEQ ID NO 7
<211> LENGTH: 20
<212> TYPE: DNA
<213> ORGANISM: homo sapiens

<400> SEQUENCE: 7
aacctcacaa ccttggctga                                                20

<210> SEQ ID NO 8
<211> LENGTH: 20
<212> TYPE: DNA
<213> ORGANISM: homo sapiens

<400> SEQUENCE: 8
ttcacaactt aagatttggc                                                20

<210> SEQ ID NO 9
<211> LENGTH: 20
<212> TYPE: DNA
<213> ORGANISM: homo sapiens

<400> SEQUENCE: 9
aggcaactag gatggtgtgg                                                20

<210> SEQ ID NO 10
<211> LENGTH: 19
<212> TYPE: DNA
<213> ORGANISM: homo sapiens

<400> SEQUENCE: 10
cagggagcgt gtccatagg                                                 19

<210> SEQ ID NO 11
<211> LENGTH: 21
<212> TYPE: DNA
<213> ORGANISM: homo sapiens

<400> SEQUENCE: 11
ctgctgaaag agatgcggtg g                                              21

<210> SEQ ID NO 12
<211> LENGTH: 22
<212> TYPE: DNA
<213> ORGANISM: homo sapiens

<400> SEQUENCE: 12
aggaaaacag cccaagggac ag                                             22

<210> SEQ ID NO 13
```

```
<211> LENGTH: 19
<212> TYPE: DNA
<213> ORGANISM: homo sapiens

<400> SEQUENCE: 13
cacatcaatg ttgttgttt                                              19

<210> SEQ ID NO 14
<211> LENGTH: 20
<212> TYPE: DNA
<213> ORGANISM: homo sapiens

<400> SEQUENCE: 14
ttccttgtct ccccaagttc                                             20

<210> SEQ ID NO 15
<211> LENGTH: 20
<212> TYPE: DNA
<213> ORGANISM: homo sapiens

<400> SEQUENCE: 15
actttgttct gagcctcaca                                             20

<210> SEQ ID NO 16
<211> LENGTH: 20
<212> TYPE: DNA
<213> ORGANISM: homo sapiens

<400> SEQUENCE: 16
gttgcccaat cgcccctctc                                             20

<210> SEQ ID NO 17
<211> LENGTH: 20
<212> TYPE: DNA
<213> ORGANISM: homo sapiens

<400> SEQUENCE: 17
aacctgacta gaaaagctat                                             20

<210> SEQ ID NO 18
<211> LENGTH: 20
<212> TYPE: DNA
<213> ORGANISM: homo sapiens

<400> SEQUENCE: 18
gaatgagtgg ttaattaatt                                             20

<210> SEQ ID NO 19
<211> LENGTH: 20
<212> TYPE: DNA
<213> ORGANISM: homo sapiens

<400> SEQUENCE: 19
ctctagcgac tgtccatctc                                             20

<210> SEQ ID NO 20
<211> LENGTH: 20
<212> TYPE: DNA
<213> ORGANISM: homo sapiens

<400> SEQUENCE: 20
gacagccacc agatccaatc                                             20
```

```
<210> SEQ ID NO 21
<211> LENGTH: 25
<212> TYPE: DNA
<213> ORGANISM: homo sapiens

<400> SEQUENCE: 21
gactactcta gcgactgtcc atctc                                           25

<210> SEQ ID NO 22
<211> LENGTH: 25
<212> TYPE: DNA
<213> ORGANISM: homo sapiens

<400> SEQUENCE: 22
gactggacag ccaccagatc caatc                                           25

<210> SEQ ID NO 23
<211> LENGTH: 30
<212> TYPE: DNA
<213> ORGANISM: homo sapiens

<400> SEQUENCE: 23
ttaaagacta ctctagcgac tgtccatctc                                      30

<210> SEQ ID NO 24
<211> LENGTH: 30
<212> TYPE: DNA
<213> ORGANISM: homo sapiens

<400> SEQUENCE: 24
cattagactg gacagccacc agatccaatc                                      30

<210> SEQ ID NO 25
<211> LENGTH: 35
<212> TYPE: DNA
<213> ORGANISM: homo sapiens

<400> SEQUENCE: 25
gtggattaaa gactactcta gcgactgtcc atctc                                35

<210> SEQ ID NO 26
<211> LENGTH: 35
<212> TYPE: DNA
<213> ORGANISM: homo sapiens

<400> SEQUENCE: 26
tatcccatta gactggacag ccaccagatc caatc                                35

<210> SEQ ID NO 27
<211> LENGTH: 40
<212> TYPE: DNA
<213> ORGANISM: homo sapiens

<400> SEQUENCE: 27
gttgtgtgga ttaaagacta ctctagcgac tgtccatctc                           40

<210> SEQ ID NO 28
<211> LENGTH: 40
<212> TYPE: DNA
<213> ORGANISM: homo sapiens

<400> SEQUENCE: 28
aatcttatcc cattagactg gacagccacc agatccaatc                           40
```

<210> SEQ ID NO 29
<211> LENGTH: 45
<212> TYPE: DNA
<213> ORGANISM: homo sapiens

<400> SEQUENCE: 29
ttcctgttgt gtggattaaa gactactcta gcgactgtcc atctc         45

<210> SEQ ID NO 30
<211> LENGTH: 45
<212> TYPE: DNA
<213> ORGANISM: homo sapiens

<400> SEQUENCE: 30
gttttaatct tatcccatta gactggacag ccaccagatc caatc         45

<210> SEQ ID NO 31
<211> LENGTH: 20
<212> TYPE: DNA
<213> ORGANISM: homo sapiens

<400> SEQUENCE: 31
gcagctttca tgggcactgt         20

<210> SEQ ID NO 32
<211> LENGTH: 20
<212> TYPE: DNA
<213> ORGANISM: homo sapiens

<400> SEQUENCE: 32
cagggctgga ctgacatttg         20

<210> SEQ ID NO 33
<211> LENGTH: 25
<212> TYPE: DNA
<213> ORGANISM: homo sapiens

<400> SEQUENCE: 33
tccaggcagc tttcatgggc actgt         25

<210> SEQ ID NO 34
<211> LENGTH: 25
<212> TYPE: DNA
<213> ORGANISM: homo sapiens

<400> SEQUENCE: 34
agagacaggg ctggactgac atttg         25

<210> SEQ ID NO 35
<211> LENGTH: 30
<212> TYPE: DNA
<213> ORGANISM: homo sapiens

<400> SEQUENCE: 35
ctacctccag gcagctttca tgggcactgt         30

<210> SEQ ID NO 36
<211> LENGTH: 30
<212> TYPE: DNA
<213> ORGANISM: homo sapiens

<400> SEQUENCE: 36
cacagagaga cagggctgga ctgacatttg         30

<210> SEQ ID NO 37
<211> LENGTH: 35
<212> TYPE: DNA
<213> ORGANISM: homo sapiens

<400> SEQUENCE: 37
gccttctacc tccaggcagc tttcatgggc actgt                          35

<210> SEQ ID NO 38
<211> LENGTH: 35
<212> TYPE: DNA
<213> ORGANISM: homo sapiens

<400> SEQUENCE: 38
gyaagcacag agagacaggg ctggactgac atttg                          35

<210> SEQ ID NO 39
<211> LENGTH: 40
<212> TYPE: DNA
<213> ORGANISM: homo sapiens

<400> SEQUENCE: 39
tctgggcctt ctacctccag gcagctttca tgggcactgt                     40

<210> SEQ ID NO 40
<211> LENGTH: 40
<212> TYPE: DNA
<213> ORGANISM: homo sapiens

<400> SEQUENCE: 40
gtggagyaag cacagagaga cagggctgga ctgacatttg                     40

<210> SEQ ID NO 41
<211> LENGTH: 45
<212> TYPE: DNA
<213> ORGANISM: homo sapiens

<400> SEQUENCE: 41
ccctgtctgg gccttctacc tccaggcagc tttcatgggc actgt                45

<210> SEQ ID NO 42
<211> LENGTH: 45
<212> TYPE: DNA
<213> ORGANISM: homo sapiens

<400> SEQUENCE: 42
atcgggtgga gyaagcacag agagacaggg ctggactgac atttg                45

<210> SEQ ID NO 43
<211> LENGTH: 22
<212> TYPE: DNA
<213> ORGANISM: homo sapiens

<400> SEQUENCE: 43
cccacgatca atgccatcaa ct                                         22

<210> SEQ ID NO 44
<211> LENGTH: 22
<212> TYPE: DNA
<213> ORGANISM: homo sapiens

<400> SEQUENCE: 44

| | |
|---|---|
| cggtgagagg cactgccaga tt | 22 |

<210> SEQ ID NO 45
<211> LENGTH: 22
<212> TYPE: DNA
<213> ORGANISM: homo sapiens

<400> SEQUENCE: 45

| | |
|---|---|
| gctcgctttc ttgctgtcca at | 22 |

<210> SEQ ID NO 46
<211> LENGTH: 24
<212> TYPE: DNA
<213> ORGANISM: homo sapiens

<400> SEQUENCE: 46

| | |
|---|---|
| gcccttcata atatccccca gttt | 24 |

<210> SEQ ID NO 47
<211> LENGTH: 20
<212> TYPE: DNA
<213> ORGANISM: homo sapiens

<400> SEQUENCE: 47

| | |
|---|---|
| gtccttcccc cgctggaaac | 20 |

<210> SEQ ID NO 48
<211> LENGTH: 20
<212> TYPE: DNA
<213> ORGANISM: homo sapiens

<400> SEQUENCE: 48

| | |
|---|---|
| gcagcagaga tcatcgcgcc | 20 |

<210> SEQ ID NO 49
<211> LENGTH: 21
<212> TYPE: DNA
<213> ORGANISM: homo sapiens

<400> SEQUENCE: 49

| | |
|---|---|
| gtgggggtgc tgggagtttg t | 21 |

<210> SEQ ID NO 50
<211> LENGTH: 23
<212> TYPE: DNA
<213> ORGANISM: homo sapiens

<400> SEQUENCE: 50

| | |
|---|---|
| tcggacagaa acatgggtct gaa | 23 |

<210> SEQ ID NO 51
<211> LENGTH: 22
<212> TYPE: DNA
<213> ORGANISM: homo sapiens

<400> SEQUENCE: 51

| | |
|---|---|
| ggtgctcaga acccccacaa tc | 22 |

<210> SEQ ID NO 52
<211> LENGTH: 22
<212> TYPE: DNA
<213> ORGANISM: homo sapiens

<400> SEQUENCE: 52

-continued cctaccgacc ccattccact ct                                        22

<210> SEQ ID NO 53
<211> LENGTH: 23
<212> TYPE: DNA
<213> ORGANISM: homo sapiens

<400> SEQUENCE: 53
cacagatttc caaggatgcg ctg                                       23

<210> SEQ ID NO 54
<211> LENGTH: 20
<212> TYPE: DNA
<213> ORGANISM: homo sapiens

<400> SEQUENCE: 54
cgtgctctgt tccagacttg                                           20

<210> SEQ ID NO 55
<211> LENGTH: 22
<212> TYPE: DNA
<213> ORGANISM: homo sapiens

<400> SEQUENCE: 55
cgtctggcga ttgctccaaa tg                                        22

<210> SEQ ID NO 56
<211> LENGTH: 22
<212> TYPE: DNA
<213> ORGANISM: homo sapiens

<400> SEQUENCE: 56
gggcagttgt gatccatgag aa                                        22

<210> SEQ ID NO 57
<211> LENGTH: 22
<212> TYPE: DNA
<213> ORGANISM: homo sapiens

<400> SEQUENCE: 57
ggcttgcacc agcttaggaa ag                                        22

<210> SEQ ID NO 58
<211> LENGTH: 25
<212> TYPE: DNA
<213> ORGANISM: homo sapiens

<400> SEQUENCE: 58
cgttaggcat aatcagtggg atagt                                     25

<210> SEQ ID NO 59
<211> LENGTH: 26
<212> TYPE: DNA
<213> ORGANISM: homo sapiens

<400> SEQUENCE: 59
gcctctgatt cctcactgat tgctct                                    26

<210> SEQ ID NO 60
<211> LENGTH: 23
<212> TYPE: DNA
<213> ORGANISM: homo sapiens

```
<400> SEQUENCE: 60
tgtcaaccac ccttaacccc tcc                                          23

<210> SEQ ID NO 61
<211> LENGTH: 22
<212> TYPE: DNA
<213> ORGANISM: homo sapiens

<400> SEQUENCE: 61
ttggaggggt gggtgagtca ag                                           22

<210> SEQ ID NO 62
<211> LENGTH: 23
<212> TYPE: DNA
<213> ORGANISM: homo sapiens

<400> SEQUENCE: 62
ggaggggtgg gggttaatgg tta                                          23

<210> SEQ ID NO 63
<211> LENGTH: 21
<212> TYPE: DNA
<213> ORGANISM: homo sapiens

<400> SEQUENCE: 63
ggaacaagac acggctgggt t                                            21

<210> SEQ ID NO 64
<211> LENGTH: 21
<212> TYPE: DNA
<213> ORGANISM: homo sapiens

<400> SEQUENCE: 64
agcaaggcag ggcaggcaag t                                            21

<210> SEQ ID NO 65
<211> LENGTH: 22
<212> TYPE: DNA
<213> ORGANISM: homo sapiens

<400> SEQUENCE: 65
cggtcccatt ctcagggaat ct                                           22

<210> SEQ ID NO 66
<211> LENGTH: 22
<212> TYPE: DNA
<213> ORGANISM: homo sapiens

<400> SEQUENCE: 66
gcccagagga agaagaagga aa                                           22
```